United States Patent [19]
Kehr

[11] Patent Number: 5,642,731
[45] Date of Patent: Jul. 1, 1997

[54] METHOD OF AND APPARATUS FOR MONITORING THE MANAGEMENT OF DISEASE

[75] Inventor: Bruce A. Kehr, Potomac, Md.

[73] Assignee: InforMedix, Inc., Rockville, Md.

[21] Appl. No.: 352,828

[22] Filed: Dec. 2, 1994

Related U.S. Application Data

[63] Continuation-in-part of Ser. No. 556,626, Jul. 23, 1990, which is a continuation-in-part of Ser. No. 464,877, Jan. 17, 1990, Pat. No. 5,200,891.

[51] Int. Cl.$^6$ .................... G04B 47/00; A61B 5/00; G06F 17/00
[52] U.S. Cl. ............................................. 128/630
[58] Field of Search ....................... 128/630, 897, 128/898; 364/413.02, 479; 221/1–3, 5, 9, 15

[56] References Cited

U.S. PATENT DOCUMENTS

| | | |
|---|---|---|
| 3,966,086 | 6/1976 | Kelso . |
| 4,186,438 | 1/1980 | Benson . |
| 4,223,801 | 9/1980 | Carlson . |
| 4,258,354 | 3/1981 | Carmon et al. . |
| 4,275,384 | 6/1981 | Hicks et al. . |
| 4,293,845 | 10/1981 | Villa-Real . |
| 4,360,125 | 11/1982 | Martindale et al. . |
| 4,361,408 | 11/1982 | Wirtschafter . |
| 4,382,688 | 5/1983 | Machamer . |
| 4,473,884 | 9/1984 | Behl . |
| 4,483,626 | 11/1984 | Noble . |
| 4,490,711 | 12/1984 | Johnston . |
| 4,588,303 | 5/1986 | Wirtschafter et al. . |
| 4,626,105 | 12/1986 | Miller . |
| 4,682,299 | 7/1987 | McIntosh et al. . |
| 4,695,954 | 9/1987 | Rose et al. . |
| 4,717,042 | 1/1988 | McLaughlin . |
| 4,725,999 | 2/1988 | Tate . |
| 4,768,176 | 8/1988 | Kehr et al. . |
| 4,768,177 | 8/1988 | Kehr et al. . |
| 4,837,719 | 6/1989 | McIntosh et al. . |
| 4,862,431 | 8/1989 | Drouin . |
| 4,879,699 | 11/1989 | Sakamoto . |
| 4,926,572 | 5/1990 | Holmes . |
| 4,962,491 | 10/1990 | Schaeffer . |
| 5,020,037 | 5/1991 | Raven . |
| 5,084,828 | 1/1992 | Kaufman et al. ............. 364/413.02 X |
| 5,088,056 | 2/1992 | McIntosh et al. ............. 364/413.02 X |
| 5,097,429 | 3/1992 | Wood et al. . |
| 5,126,957 | 6/1992 | Kaufman et al. ............. 364/413.02 X |
| 5,408,443 | 4/1995 | Weinberger ...................... 221/3 X |

OTHER PUBLICATIONS

Patient Computers to Enhance Compliance with Completing Questionnaires: A challenge for the 1990's, Bengt Dahlstrom and Sven–Ake Eckernas in Patient Compliance in Medical Practice and Clinical Trails edited by J.A. Cramer and B. Spilker, Raven Press, Ltd. New York, 1991.

*Primary Examiner*—Lee S. Cohen
*Assistant Examiner*—Samuel Gilbert
*Attorney, Agent, or Firm*—William D. Hall

[57] ABSTRACT

The present invention monitors the disease process and health of a patient undergoing drug treatment. A microprocessor-based medication dispenser provides for recording a variety of clinical information data; such as illness symptoms, side effects, general health ratings, adverse drug interactions, illness attitudes, and lifestyle habits at various times during a drug delivery cycle. The date and time of entry of the specific clinical information is entered, and correlated with the date and time when the patient has taken or missed a particular medication. The effects of the presumptive blood levels of one or more medications can then be assessed, as to their impact on the disease process, and any additional effects on the body. The device can analyze the data and display a response to it, or download the data into another device. The second device can analyze the data, and upload new information into the first device, to tell the patient to alter his or her behavior in taking medication. In this fashion, better disease management will occur.

57 Claims, 29 Drawing Sheets

Fig.31

9500 Push ON/OFF button 99 to ON

9501 First Diagnostic Question is displayed along with "YES" and "NO" buttons.

9507 Press "ON/OFF" button 99 to exit.

9502 Press "YES" and next question regarding this particular diagnosis is displayed along with "YES" and "NO" buttons.

9503 Press "NO" and screen displays diagnostic question for a different illness along with "YES" and "NO" buttons.

9504 By pressing "YES" or "NO" buttons the device will display various routines that branch to an end-message advising the patient.

9506 By pressing "YES" or "NO" buttons the device will display various routines that branch to a different end-message advising the patient.

9505 Press "ON/OFF" button 99 to turn OFF display.

METHOD OF AND APPARATUS FOR MONITORING THE MANAGEMENT OF DISEASE

RELATED APPLICATIONS

This application is a continuation-in-part application of my prior copending application Ser. No. 07/556,626 filed Jul. 23, 1990, and entitled Electronic Medication Monitoring and Dispensing Method, which is in turn a continuation-in-part of application Ser. No. 07/464,877, filed Jan. 17, 1990, now U.S. Pat. No. 5,200,891.

BACKGROUND OF THE INVENTION

There are a number of prior art patents that disclose medicine dispensing devices that alert the patient at the time or times each day that the medication should be taken. Some of those patents also disclose the concept of advising the patient's physician and/or pharmacist of any non-compliance with the scheduled medication routine.

Typical United States patents along the lines described above include:

| | |
|---|---|
| Carlson | 4,223,801 |
| Cannon | 4,258,354 |
| McIntosh | 4,682,299 |
| Rose | 4,695,954 |
| Urquhart | 4,725,997 |
| Kehr | 4,768,177 |
| Schaeffer | 4,962,491 |

SUMMARY OF THE INVENTION

In disease management, medication compliance is not the most critical factor to measure and manage. The critical issue is rather how the patient's body responds to a particular drug or combination of drugs, at a specific dosage and frequency of drug administration, at specific times throughout the drug delivery cycle. The response of illness symptoms to drug treatment, the occurrence of side-effects, and the development of adverse drug interactions depend in large part upon the level of the drug in the patient's body. If the level is too low, the symptoms generally worsen; if the level is too high, or if multiple drugs are used at one time, side-effects or adverse reactions are much more likely to occur. The science of clinical pharmacology studies how a given drug behaves throughout a range of blood levels of the drug in the body, and how it behaves along with other drugs being taken by the patient.

When any given drug enters the patient, its level rises, then falls over a given time period characteristic for that drug, for that particular patient. This time period is the drug delivery cycle. These blood levels are affected by a variety of factors including the patient's genetic makeup, time-of-day, other drugs taken, relationship to a meal, etc. The limitations of paper and pencil or computer-based patient questionnaires is that they do not sample important data about the patient's clinical response to drugs at preselected times throughout the drug delivery cycle, for a particular drug or multiple drugs regimens. They also cannot cross-correlate patient medication compliance, partial compliance, or noncompliance with: concomitant variations in the blood levels of the drug or drugs; with the outcomes of the patient's illness and symptoms; and with the incidence of side-effects and adverse reactions. Without this cross-correlation of compliance data for one or more drugs with specific measures of disease outcome, proper evaluation of the effectiveness and side-effects of drugs is not possible. In addition, such measures have traditionally depended upon the retrospective recall of the patient.

The other problem with such traditional methods is that they can't account for the "white coat effect." The "white coat effect" is the well-described tendency for many patients to want to please their doctor by falsifying information at the time of the interview with the doctor. They will overestimate their medication compliance, overestimate the positive effects of their drug treatment; and deny or minimize the negative effects of the drug, or claim that they have been fully compliant with the drug therapy regimen.

Conversely, some patients who are very dependent on their doctors do not want to get better, as then the doctor won't recommend another visit. These dependent patients come in to see the doctor and exaggerate their complaints, and minimize the positive effects of the drugs, to ensure that the doctor will remain an active caretaker in their lives. If one could gather clinical information about the patient while simultaneously gathering medication compliance data, at multiple times far removed from the visit with the doctor, and at multiple points throughout the drug delivery cycle, for one or more drugs, a much more accurate picture will emerge of the actual effects of different drug levels and combinations of drugs on the patient's clinical condition, without the "white coat effect."

Such a method could also establish that many patient complaints such as "the drug makes me sick all the time," are actually side-effects that only occur during a limited time period in the drug delivery cycle, such as during peak blood levels of the drug. In this case, armed with this information, the doctor could lower the drug dose and eliminate the side-effects, while preserving the positive effects of the drug. Under traditional measures of assessment, the doctor would take the patient off the drug, concluding that since the side-effects were so pervasive, this was the only solution.

The present invention provides for the "real time" monitoring of disease response, side-effects, medication compliance and other variables throughout all phases of the drug delivery cycle. It also provides for the duration of illness symptoms and side-effects, as well as their severity. It provides this for a single medication, or for multiple medications taken by a single patient. Multiple medications increase the likelihood of serious or fatal drug interactions for the patient. The capacity to simultaneously gather compliance data for each medication in a multiple medication regimen, along with clinical data, side-effects, and adverse drug interactions, can be lifesaving. This capacity is unavailable through prior art.

The present device has the capacity to capture all of the above data at an unlimited number of data points throughout the drug delivery cycle, for multiple medications. By capturing clinical, psychological, and lifestyle data at multiple data points, along with compliance data, the dose and frequency regimen for each medication can be correlated with each aspect of the other data captured. From this a pharmacologic "profile" of a single drug or infinite combinations of drugs can be developed relating: each phase of the drug(s) in the drug delivery cycle (peak blood level, trough blood level, absence of drug, etc); to the effects of the drug on illness symptoms at that phase; to effects of the drug in causing side-effects at that phase; to the incidence of adverse reactions at that phase; and to other important clinical data.

As most drugs bind to organ receptors in the body to treat illness (and cause side-effects), this pharmacologic "profile" can be used to better understand the effects of different drug levels, and different combinations of drugs at different levels, on these receptors.

Prior art also cannot address what appears to be a simple question, whose answer carries profound implications; "What percent compliance with a drug treatment regimen (dose of drug, number taken, and frequency of taking) produces optimum treatment for a disease, with minimum side-effects?" For some drugs this may be 100% compliance. For others it may be 80%. For others it may be 50%. These percentages can vary from patient to patient. They can also vary within a patient, as the addition or deletion of a second or third drug can alter the blood levels of the first drug. By simultaneously monitoring, in one device, the compliance with each drug regimen along with the response of illness symptoms, the present invention can answer the above question.

It is also desirable, during the course of treating an illness, to give advice to the patient about what to do next, and what to do differently. The doctor is not always available to give this advice, or may not know what to advise. In the present invention, the data captured at various data points can be downloaded into a computer for analysis, and for comparison with a database. Through such comparison with prior data in a database; the computer can upload into the present device new information, to assist the patient in taking the drugs differently; or in better understanding why they need to take a drug in a way they haven't been taking it; or by providing new information to the patient about the drug or disease being treated; or other information. This newly uploaded, databased information can encourage the patient to alter their behavior in a particular way, or confirm that the patient's medication taking is proper, by praising the patient.

In addition, information stored in the device can be displayed graphically or pictorially on its display; or downloaded into a computer, which can analyze the data and then upload the conclusions from the analysis for graphic or pictorial display on the device. This display can indicate to the patient the progress being made in treating the illness, a worsening of the illness related to noncompliance, or display other trend information for ready comprehension by the patient. Such data analysis can also warn the patient that a worrisome trend or adverse reaction is developing, and instruct them what to do next. For example, for the patient who is only partially compliant with their anti-epileptic medication, who develops a new symptom that forewarns the development of a seizure, the device could display a human figure falling on the ground, as if in a seizure.

At times a patient undergoing drug treatment may develop symptoms of a new illness, related or unrelated to the previous illness. For example, certain drugs can cause colitis, or mimic symptoms of a heart attack. It would be helpful, therefore, to provide the device with a self-diagnosis algorithm. The algorithm would enable the patient to answer certain diagnostic questions, and lead to a conclusion regarding what new illness may be developing, and what to do about it. By correlating compliance data with the algorithm, the contribution of particular drugs at particular dosages in causing the new illness could be assessed. This is crucial data to gather. Witness recently the withdrawal from the market of a new and highly effective anticonvulsant—Felbatrol—after two patients developed a fatal anemia while on the drug. The present invention could have answered vital questions about what happened such as: "What doses of Felbatrol were the deceased patients actually taking?" "Were they taking too much?" "What early symptoms or side-effects did they develop prior to the fatal anemia?" "What other drugs were they taking, when, and in what dosages?" Only the present invention could answer these vital questions, which may have allowed other patients who needed the Felbatrol, and who did not fit the "fatality profile," to stay on the drug.

At times a patient fails to take a drug at the scheduled time. It would be helpful to know why. Were they having an unacceptable side-effect at the time, and therefore not inclined to take the drug? Were they feeling better at the time, and therefore believed that they didn't need any more drug? The present device, unlike prior art, can answer these questions by prompting the patient to respond to questions about symptoms and side-effects at a time when the patient misses a scheduled dose.

At other times a patient takes a pill at an unscheduled time. It would be helpful to know if at that time they were having a flare-up of illness symptoms, or generally felt more ill. The present device can answer these questions by providing illness symptom ratings and general health questions at a time of unscheduled medication taking. No prior art reference can do this.

Certain less tangible or intangible characteristics of the patient also affect the outcome of disease treatments. Factors such as attitude toward the illness, attitude toward treatment, motivation to pet better and trust affect treatment outcomes. So can lifestyle habits such as diet, exercise, smoking and drinking. The present device can query the patient on these factors, and provide correlative analysis with compliance data, and other clinical data. Conclusions can then be drawn about the effects of drugs on disease along with psychological aspects of the patient; and conversely the effects of psychological factors on medication compliance and disease outcome. No prior art does this.

Finally, the device must be easy to program, easy to use, and provide for a wide variety of applications. The device can be programmed with information common to all diseases and drugs. In addition, it can be programmed with information related to specific drugs or illnesses, through plug-in software modules that "customize" the information for the particular patient.

Data entry for all of the clinical parameters noted above can be facilitated by a programmable touch-screen, that displays questions and information, and provides for adjacent touch-points to enter the data. The screen can also display pictures to warn the patient about the outcome of certain undesired medication-taking behaviors, or praise and amuse the patient with pictures related to desired medication-taking behavior.

Thus, the present invention provides a powerful new tool for disease management programs in managed care, and for clinical drug trials. By providing cross-correlation of compliance data for multiple medications, with outcomes measures of disease response, at all phases of the drug delivery cycle; and by providing for databased analysis and display of new information on the device, based upon the patient's behavior, and the behavior of his or her illness and body in response to the drugs; optimization of drug treatments will occur to bring about more effective, and cost-effective treatment of disease.

BRIEF DESCRIPTION OF THE DRAWINGS

FIG. 31 is a flow chart of the SELF-DIAGNOSIS routine.

DETAILED DESCRIPTION OF THE INVENTION

Figure 1:
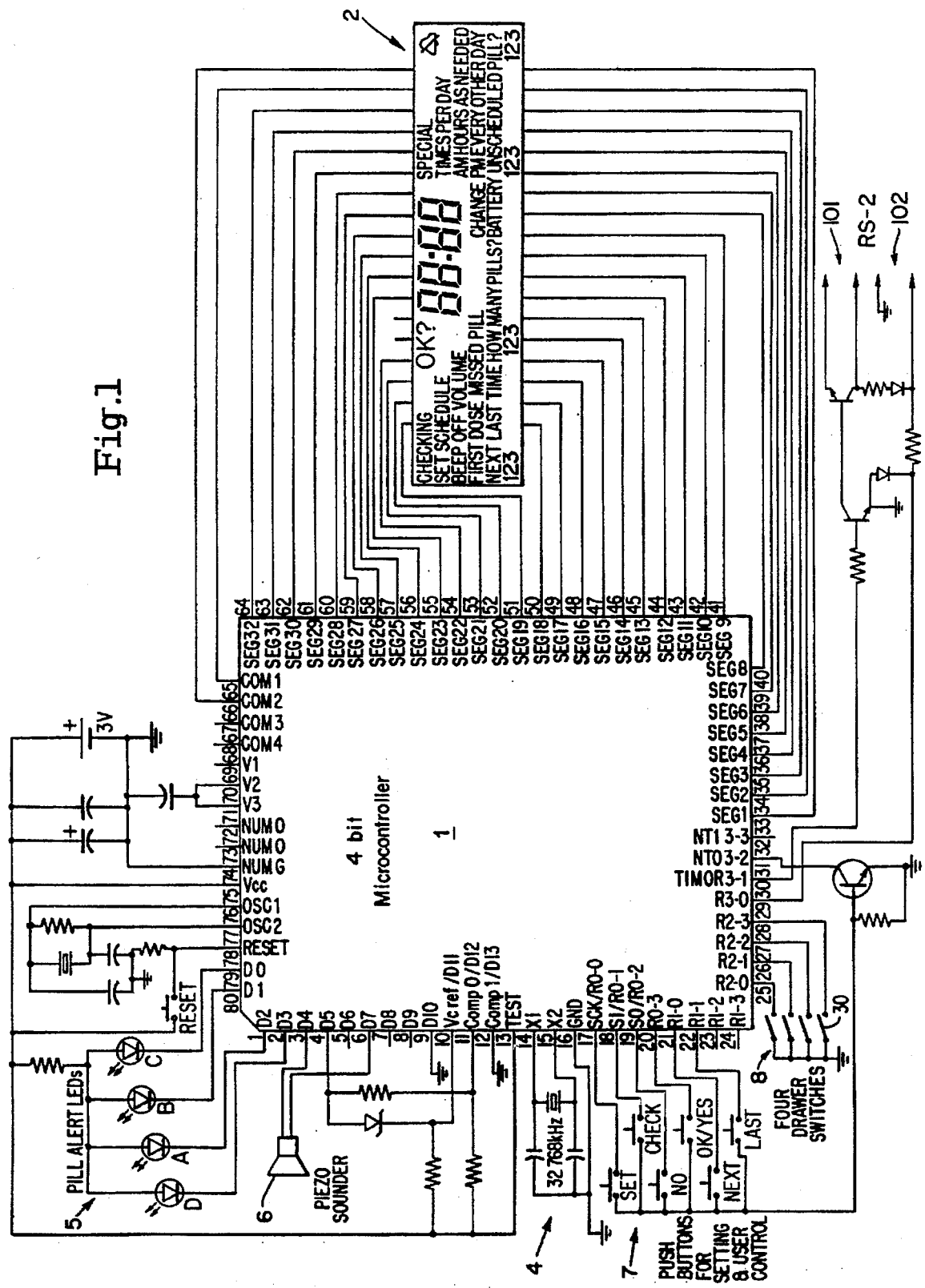
FIG. 1 is a schematic diagram of the microprocessor and associated circuitry.

As illustrated in FIG. 1, the present invention utilizes an Hitachi Model HD4074808 microprocessor chip 1 for accepting user inputs and for performing the necessary logic for driving the liquid crystal display 2 and associated medication alert signals.

The microcontroller 1 is a MCU microcomputer utilizing a 4-bit architecture and having built-in ROM and RAM. The chip includes a 16 digit LCD driver and 30 I/O pins. The microcontroller 1 is also provided with a crystal oscillator circuit 3 for supplying the internal clock and timing circuits for proper operation of the microprocessor 1. The chip is also provided with a clock crystal circuit 4 to enable the chip to accurately track the time of day in order to display the necessary medication alerts at the appropriate times.

The microcontroller continually operates in a low power mode with a 32 kHz clock crystal, and each half second an interrupt is generated to change the state of the colon (such that the colon is continually blinking, on for one half second and then off for one half second), incrementing the time keeping circuitry and keeping track of the time of day. The time of day may be shown on the unit's display. The time of day is continually compared against the scheduled medication times, and, when a match is found, an output of the microcontroller is enabled to turn on the light associated with the appropriate compartment, and other outputs are set to enable the audible signal and to show the number of pills on the display associated with that compartment.

In addition to the liquid crystal display 2, a series of light-emitting diodes (LEDs) A–D are provided in circuit 5, which, along with Piezo buzzer 6 are, attached to I/O ports of the microcontroller 1.

As an alternative to the display LCD 2, one could use an alpha-numeric LCD display, that can display a large variety of messages and questions related to the medications contained within the compartments; including additional dosing information; questions regarding illness symptoms, medication side effects, general health, or adverse drug reactions; said messages could also instruct the patient as to which buttons to push at selected times, to facilitate entry of the patient's answers to the questions into the memory of the device.

Instead of a liquid crystal display, a Bit-Map or Pixil display can be substituted. The Bit-Map display would allow for an almost infinite number of messages and questions to be displayed, circumventing the limited message capacity of the liquid crystal display. Answers to the questions, and a record of the medications taken and missed, along with the date and time each bit of data is entered, are stored in the memory. As an example of such a display, the device could use the same display as used in the Franklin Digital Book System, Franklin Electronic Publishers, Mount Holly, N.J. 08060.

A series of push buttons 7, as well as a series of drawer switches 8, are connected to the 4-bit I/O ports of microcontroller 1. The liquid crystal display 2 is attached to the segment driver pins of the microcontroller 1.

Figure 5:
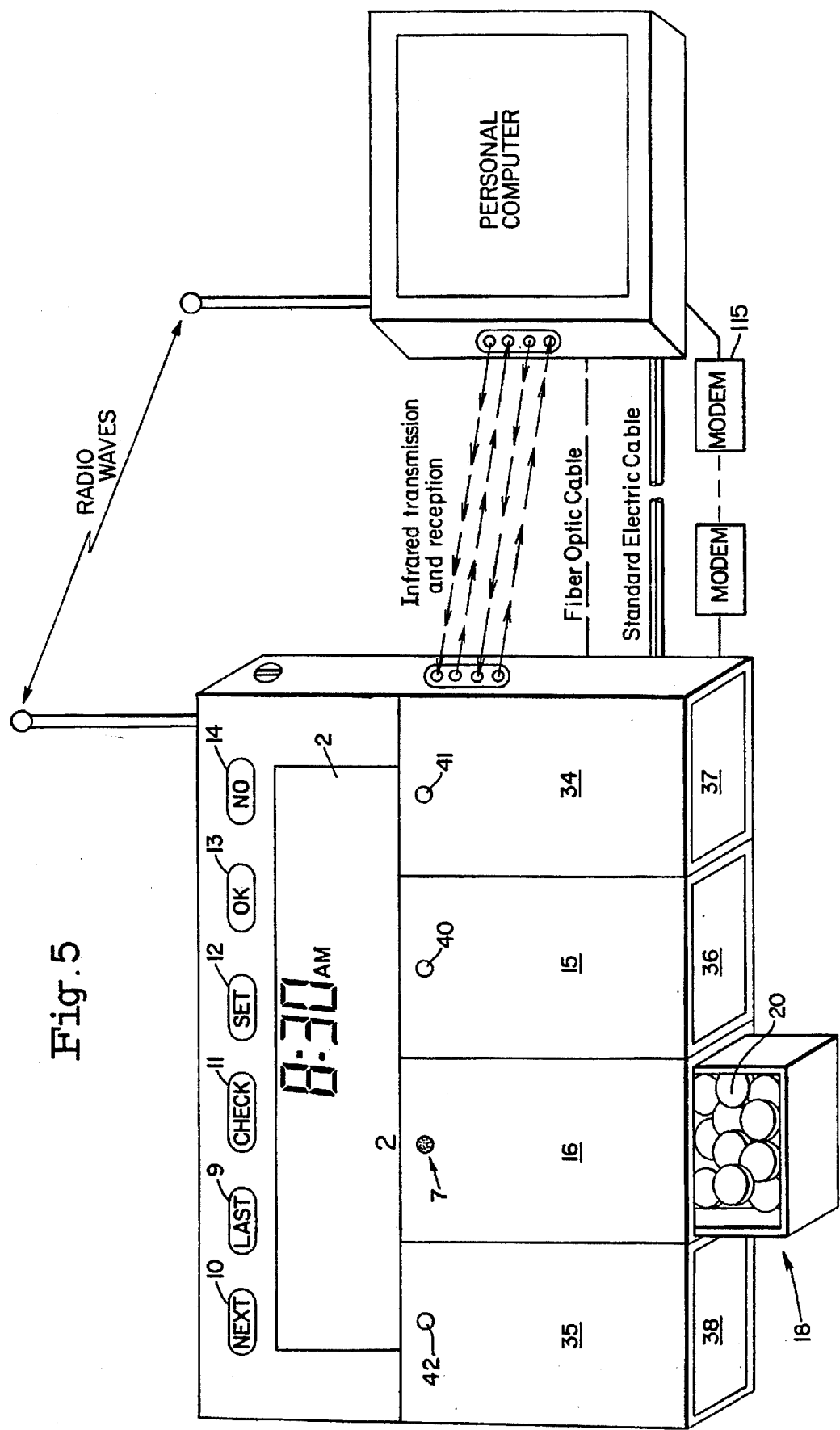
FIG. 5 is a view of the medical monitor of this invention showing how it may communicate with a remote computer.

As shown in FIGS. 1 and 5, an input 101 permits the computer of a physician, pharmacist, managed care, or pharmaceutical manufacturer to transmit information to the microprocessor 1 for storage in the memory of the microprocessor, and subsequent display on command. Similarly, there is an output 102 which permits the user of the device to download the previously stored information from the memory of microprocessor 1 to the computer of the physician, pharmacist, managed care company or pharmaceutical manufacturer.

The monitor allows for interaction with physicians or pharmacists, who can upload information into the device, or download information from the device. The data that is stored in the monitor, enumerated above, can be downloaded into a personal computer or printer. The personal computer can be programmed to analyze the data that is downloaded, and then upload information in response to the information that was downloaded. The uploaded information could include warnings to the patient regarding dangerous behavior patterns of medication taking that have been recorded by the device, or other instructions to the patient based upon analysis of patient noncompliance, partial compliance, or potential drug interactions. For example, if the patient forgets to take the medicine Digoxin for heart disease, the device might display "TO AVOID HEART FAILURE YOU MUST TAKE DIGOXIN ON TIME!"

Through the use of a Bit-Map display, a variety of messages can be given to the patient that have been uploaded from the personal computer. In addition, further instructions regarding proper medication taking (a counselling function) can be displayed to the patient to praise or correct the patient's behaviors that have been recorded and analyzed. For example, "YOU ARE DOING A GOOD JOB IN TAKING YOUR VERAPAMIL FOR THAT HIGH BLOOD PRESSURE!" Finally, the pharmacist or physician could upload into the device general information regarding the patient's illnesses that have been diagnosed, and how the particular drugs contained in the device are helpful in treating these illnesses. This general information about the illness could be displayed at the time the device gives a medication alert signal, for the particular medication that has been prescribed to treat the particular illness, or at any time the patient selects. Medical research has shown that patients are more likely to take their medications properly when they understand what their underlying illness is, why they need to take the medication, and when they get positive and negative feedback about how they are performing in taking their medications.

This information can, as shown in FIG. 5, be uploaded into the medication device via infrared beams, radio communication, electric cable, fiber optic cable, or over telephone lines via modem from the physician's or pharmacist's computer into the device. A suitable modem 115 (FIG. 5) is manufactured by Valtronic USA, Inc., 6168 Cochran Road, Solon, Ohio, 44139, phone number 216-349-1239. It is a battery operated modem that clips onto a telephone handset.

All of the above information can be uploaded into the device, including the side-effects for the medications contained in the device; potential drug interactions between the medications contained in the device, or with other medications: the specific diagnoses of illnesses from which the patient suffers; educational information about the illness, and the drugs contained in the device used to treat it; and the common symptoms that the patient may have as a result of each of these illnesses. As a result of the device recording information, displaying information, and downloading and uploading information, the patient, the computers, and the pharmacist or physician all interact together. This facilitates better communication about the medications in the device. In this way the patient education, medication counseling, and technology can all interact in a synergistic fashion to improve medication compliance, and disease management.

Figure 3:
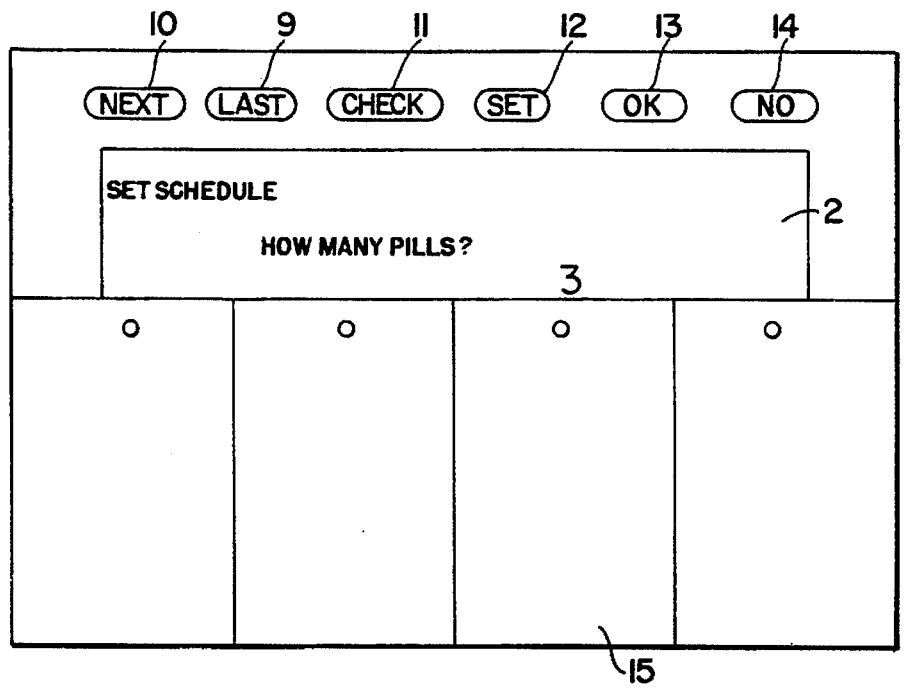
FIG. 3 is a top view of the medical monitor of the invention with all drawers closed.
Figure 4:
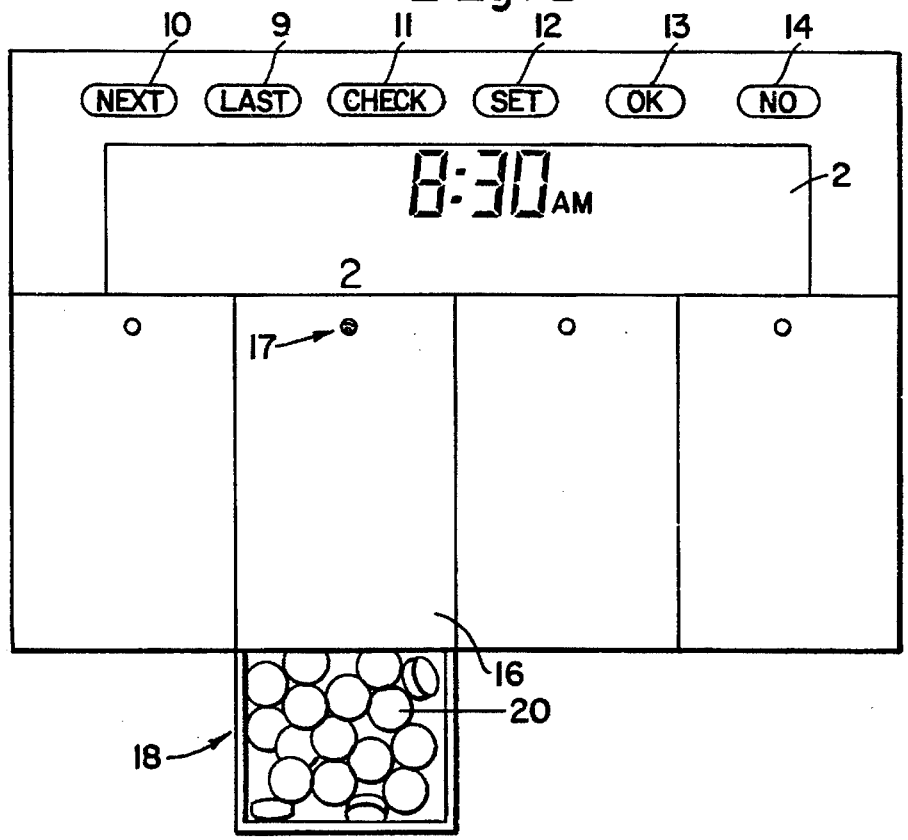
FIG. 4 is a top view as shown in FIG. 3 except that one drawer is open.

The pill box itself, as illustrated in FIGS. 3 and 4, has a top face on which is positioned the LCD display 2 as well as push buttons 9, 10, 11, 12, 13 and 14. During programming, the LCD display will display a variety of messages. One see of messages is utilized to prompt the user into providing appropriate information to the microprocessor 1. This information is needed by the monitor to establish the appropriate medication schedule. FIG. 3 illustrates an example of the monitor displaying a request for user inputs in the "set schedule" mode displaying the prompt "How many pills?" to request a pill number input from the user.

The pill number "3" is also currently displayed above the third pill box compartment 15, indicating a response from the user. If this setting were accepted, that would instruct the monitor to remind the user to take three pills from compartment 15 at a designated time. As discussed in greater detail below, the number of pills, the medication alert time and the designated compartment can be selected through the operation of push buttons 9–14.

In FIG. 4, the time of day is displayed on the LCD display 2 as well as a digit "2" above compartment 16. Further, the LED 17 associated with compartment 16 is actuated. This combination of an actuated LED 17 and a display of a digit "2" is an indication to the user that two pills should be taken from the drawer 18 located within compartment 16. The drawer 18 is illustrated in the open position exposing pills 20 therein so that they may be taken by the user.

Figure 2A:
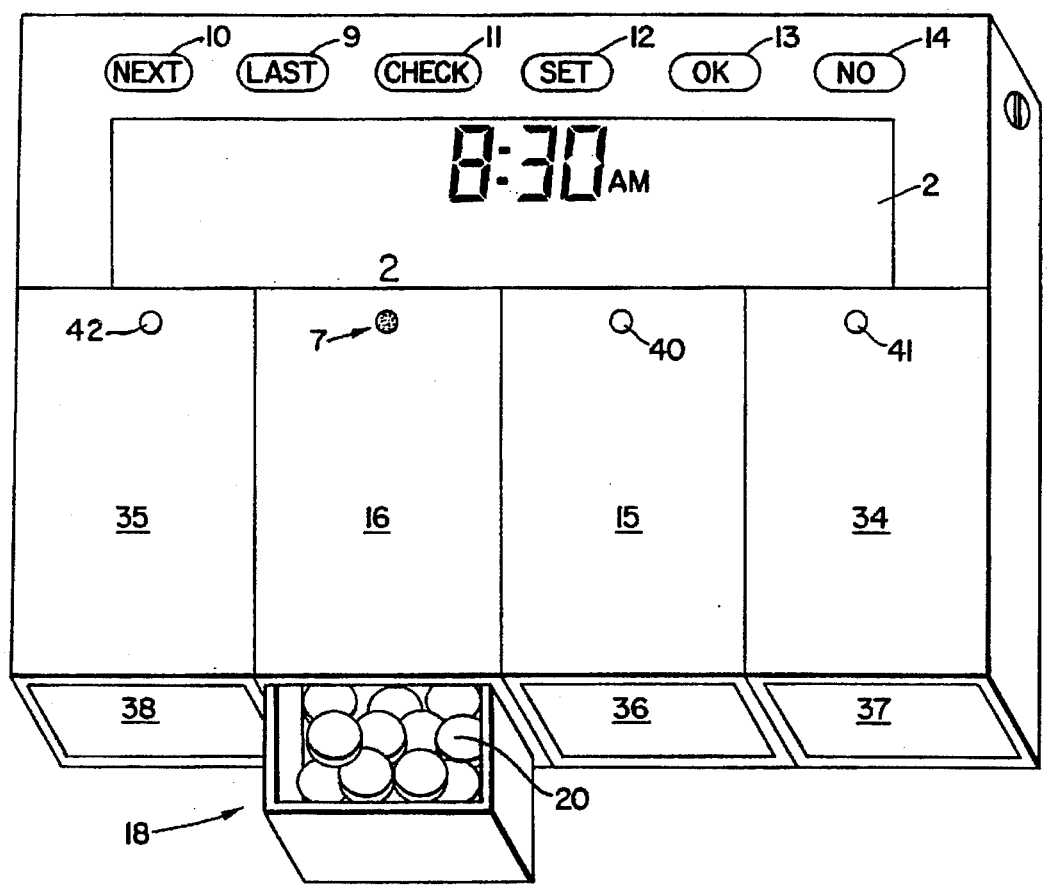
FIG. 2A to 2F are top views of devices embodying the invention.

FIG. 2A illustrates an exemplary embodiment of the monitor with four compartments, 16, 15, 34 and 35, each compartment having a drawer 20, 36, 37, 38 and an LED 17, 40 41, 42 respectively. The user is prompted to open a designated drawer in a designated compartment by activation of the LED corresponding to the appropriate compartment.

A switch 8 is associated with each of the four drawers. Each switch 8 closes when the drawer is opened. When a drawer is closed, its complementary switch 8 opens. These switches 8 may be constructed as shown in FIGS. 5A to 5D of U.S. Pat. No. 5,200,891, and are electrically connected as taught in FIG. 1.

The device provides visual signals to prompt the user during input of a medication schedule or schedules. The device then relies upon that schedule(s) to indicate to the user when medication is to be taken by providing audible and/or visual medication alert signals. The device indicates the compartment of the device from which the medication is to be taken and the quantity of medication. The compartment indication is provided by illuminating a light closely associated with the desired compartment. A liquid crystal or other type of display "2" indicates the quantity to take; i.e. if three pills are to be taken, the number "3" or "3 Pills" or "Take 3 Pills" will be displayed adjacent to the appropriate compartment.

If the patient obeys the commands of the system and opens the designated compartment, the signals and lights will be turned off until the next medication alert time arrives. The unit can optionally be designed to turn off the alert after the drawer is closed. The drawers, as well as the sides or bottoms of the compartments, may be made transparent in order to allow the user to visually check if any pills are in the compartment and to determine the type of medication, if any is present. The drawers, when opened, reveal their entire length, and have a sloped front, allowing easy access for the patient who may have tremor, arthritis or other difficulties.

If the patient fails to obey the commands of the system and does not open and close each designated compartment within a predetermined interval of time, the audible signal will continue at predetermined periodic intervals, and a visual indication will be provided (e.g. "MISSED MEDICATION"), informing the patient that he forgot to access the appropriate compartment(s), which compartment (s) he forgot to access, and how much medication he forgot to take. Other messages may be displayed that warn the patient of the adverse consequences that may result from missing the medication, such as specific illness symptoms that will flare up. The visual alarm and the lights will then be shut off when the designated compartment is opened. The patient may also indicate to the unit that he will be skipping that medication, and the alarm will be cleared.

Generally, any single medication is to be taken periodically throughout the day. The most common schedules will be available within the unit for selection by the user (e.g. once every other day, once per day, twice per day, three times per day, four times per day). The user may also provide a first dose time. If, for example, the user selects "four times per day", the first alarm will sound at the user selected first dose time, and three subsequent alarms scheduled in this manner will be shifted to match the new first dose time.

Each compartment may be independently set for one of these standard schedules, or the patient may enter a "special" schedule of up to 15 specific clock times per day that pills should be taken from a given compartment. In this manner, the most common schedules may be set very simply, but the unit is flexible enough to accommodate patients with more complex requirements.

By providing built-in programming which understands the multiple times per day format, the device automatically displays doctor's instructions and translates these into specific pill-taking times and quantity indications. This is accomplished through the user programming the device by entering the instructions as written by the physician, (e.g. "three pills four times per day,") onto the display of the monitor, and specifying a given compartment. Through the push of a button, the device then automatically, in conformance with its built-in program, translates this into a set of medication alarms such as 8:00 AM, Noon, 4:00 PM and 8:00 PM. The device also allows for specific programming of pills which need to be taken with meals or at bedtime by allowing the user to enter into the microprocessor 1, the patient's usual mealtimes or bedtime. The device also provides for labels adjacent each compartment specifying the physician's instructions, so that the instructions displayed for a specific compartment can be compared to the information on the respective label.

The use of a LCD screen allows the patient to be visually prompted during both the programming operation and the medication alert operation of the device. The built-in programming of the device also accommodates a number of confirmation steps, allowing the patient or user to doublecheck the entries before they are stored into the device, which provides for more accurate medication monitoring. The many programmable schedule options of the device allow for instructions for "every other day" medication in addition to multiple medications on a given day.

The prompt-then-record system, is taught by the monitor of the present invention. Here the device does not record an instruction until it is confirmed; and requires a response or acknowledgment to a prompt, (such as a medication alert) prior to recordation so that the event may be recorded as an "acknowledged" or "unacknowledged" event to indicate pills taken or missed, thereby increasing the accuracy of the medication monitoring. The prompt-then-record can also be utilized to record and indicate other abnormalities in the medication schedule, or record data regarding symptoms, side effects, or other clinical information previously described.

The device has a number of manually operable switches or buttons 9, 10, 11, 12, 13, 14 on the front panel of the device adjacent the display. The first two buttons 9, 10 of the display are the "Next" and "Last" buttons, described in more detail below, which allow prospective and retrospective review of the medication schedule, respectively. These buttons also allow cycling forward or backward through the different options in the various programs available within the device, such as the time of day options described above. Providing the "Next" and "Last" buttons allows ease of programming over devices which simply provide for a common mode cycling button, while allowing for simplified design over devices which require multiple buttons, each for a specific task. The patient can readily master the next/last sequencing logic which carries throughout the various programming modes where these buttons are utilized in a common manner.

The next group of buttons is the "Check and Set" buttons. The "Check" button 11 allows cycling between the different modes of the apparatus, e.g., time of day, first dose time, compartment scheduling, etc. The "Set" button 12 allows the patient or user to enter one of these programming modes and then alter the programming within the mode. By closely associating these two buttons, the patient or user readily becomes familiar with their interaction and therefore, the programming is made more easily accessible.

The last set of buttons is the "Yes/Okay" and "No" buttons 13 and 14. These buttons are utilized by the patient to answer queries' or provide acknowledgements.

A final button, the "no-bell" button, allows the patient to suspend the audible tone for predetermined time periods.

As stated above, the visual and audible medication alert signals are turned off when the patient opens the compartment. This operation is carried out by having a separate closure (for example a lid) for opening and closing each compartment, or by providing drawers within each compartment which slide out for access. When the lid or drawer is moved to open the compartment, a switch operating through the electrical circuitry of the signal system, turns off the visual medication alert signal and/or the audible alarm.

The electronic circuitry of the unit may be realized in many ways. One embodiment using a 4-bit microcontroller integrated circuit, the Hitachi HD407L4808, and some associated components, such as light emitting diodes (LEDs), a liquid crystal display (LCD), resistors, capacitors, batteries, etc., is illustrated.

The microcontroller continually operates in a low power mode with a 32 kHz clock crystal, and each half second an interrupt is generated to change the state of the colon (such that the colon is continually blinking, on for one half second and then off for one half second), incrementing the time keeping circuitry and keeping track of the time of day. The time of day may be shown on the unit's display. The time of day is continually compared against the scheduled medication times, and, when a match is found, an output of the microcontroller 1 is enabled to turn on the light associated with the appropriate compartment, and other outputs are set to enable the audible signal and to show the number of pills on the display associated with that compartment.

The opening and closing of the various compartments 20, 36, 37, 38 is sensed by the microprocessor through the actuation of individual switches associated with each compartment. Each medication alert and associated taking or skipping of medication is stored in the microcontroller's random access memory (RAM), so that the patient can later review when and if pills were presumably taken or skipped.

If desired, the audible signal may include the use of a transducer which emits speech giving special instructions to the patient relating to the taking of the medication.

By pushing a single button, the patient may, at any time, examine the schedule of medications to be taken over the next period (e.g., 24 hours), By pressing another button, the patient may review the actual times that doors were opened (and medication presumably taken) over the previous period (e.g. 24 hours, 30 days, etc.). The memory storing the prospective and retrospective information may be extended, by use of additional RAM, to provide a longer time period for review, and an electronic output 102 may be provided so this information can be directly transferred to a computer or to a printer for analysis by a pharmacist, physician, family member or other interested party.

If a compartment is opened when no pill is scheduled, the unit "chirps", and displays a question to the patient to determine if he is taking an unscheduled pill, in order to prevent the unit from recording that a pill was taken when a patient merely opens a door to check the pills or to refill a compartment. If the patient responds negatively or does not respond at all, the compartment opening is not recorded and the device assumes that the compartment was opened for checking or refill. The unscheduled pill taking is recorded in the unit's memory only if the patient responds positively.

During programming, the unit can also display specific doctors orders on the LCD and query the patient as to whether what the patient is programming is in conformance with those orders.

The unit can also display a specified medication identification on the LCD for the user to compare against the medication bottle, or label on the medication compartment, and indicate if it is the same by supplying a "YES/OKAY" or "NO" answer to the device. If the user selects "YES," the identification is stored. If "NO," the display is altered until the desired identification is displayed.

By pushing a button, the patient can suspend the audible alarm. Each push of the button suspends the audible alarm for a predetermined time period (e.g. one hour). The LCD displays a symbol that indicates that the audible tone has been suspended, while the visual alarms and prompts continue to operate as programmed. If the patient is going into a concert or meeting and does not want the device to interrupt, he can suspend the audible alarm. When he leaves the concert and references the device, it will indicate the type and quantity of medication missed and when it was scheduled, via the visual means which was not suspended.

The volume of the audible tone can also be programmed in by the patient to suit their wishes.

One button allows the patient to review and display what has been programmed into the device. With any display then showing, the push of a second button allows the device to enter the "programming mode" wherein the particular program displayed can be altered through the push of other buttons. In this programming mode, the device queries the patient as to whether each new program displayed is "OKAY," and patient can indicate "YES/OKAY" or "NO". "YES/OKAY" enters the new program into the device. Pressing "no" allows the patient to push buttons to display yet a different program on the device, until the correct program is displayed, wherein the pressing of the "YES/OKAY" button 13 then locks in the correct program into the device. This sequential pushing of buttons to reprogram the device helps to prevent inadvertent alteration of the programming (e.g. through buttons being pushed by a child or inadvertently pushed when the device is placed in a handbag).

At any time if the programming routine is interrupted for more than one minute, or if buttons are pushed inadvertently, the device will automatically return to "time of day," and the interrupted programming will not be entered, as the user did not press the "YES/OKAY" button 13.

When the compartment 18 is open and its switch closed, the microprocessor 1 is instructed to discontinue the medication alert signal such as that illustrated in FIG. 4. The time at which the switch 8 was closed, indicating the opening of the compartment 18, is stored in the microcontroller's random access memory (RAM). Each time the drawer is opened, the time of opening and the particular drawer opened is recorded in the microcontroller's RAM. If a take medication signal is generated and the corresponding drawer is not opened at that time or within a predetermined time period thereafter, this is also stored in the microcontroller's RAM as a missed pill event, along with an indication of time and the number of pills that should have been taken, with an indication that the corresponding drawer was not opened at that time. All of the information is stored in the RAM so that it can later be accessed by the user to review the taking of medication and the missing of medication.

The microcontroller 1 keeps track of time and updates the time of day display on the LCD display unit 2. The current time of day of the microprocessor 1 is continually compared against the stored times for scheduled medication. When this comparison generates a match between the stored scheduled medication times and the actual time of day, the microcontroller 1 enables one of the output terminals to the appropriate LED of the LED set 5. Simultaneously, the corresponding segment driver outputs are enabled to indicate the number of pills that should be taken from the designated compartment at that medication time. Further, if enabled by the user, the audible alarm is also triggered.

Figure 6:
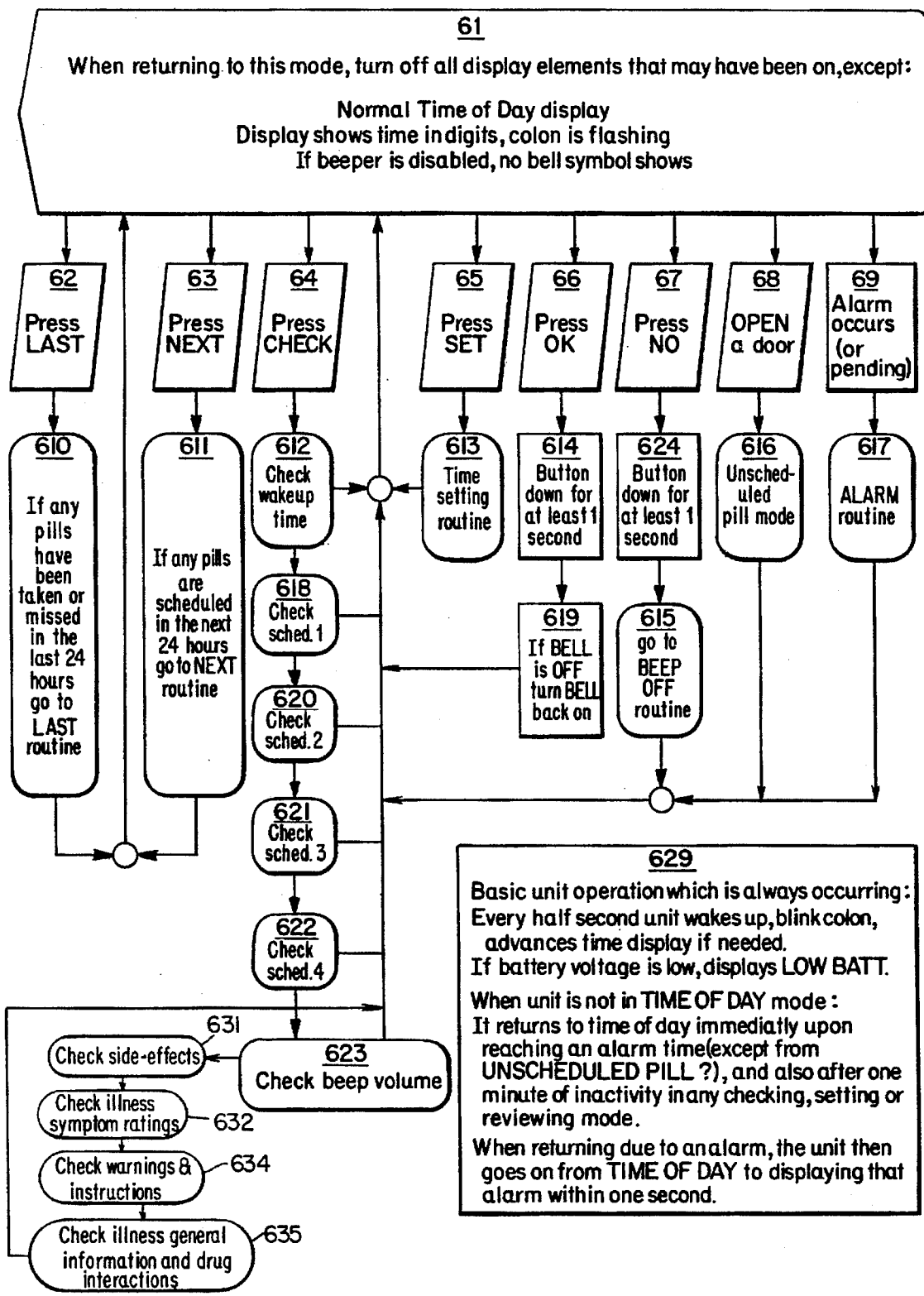
FIG. 6 is a flow chart showing the "Time of Day" mode of operation, including each of the modes of the device, available for programming.

The logical operation of the microcontroller will now be described with reference to FIGS. 6–16. FIG. 6 is an overview of the logical operation of the various monitoring routines of the monitor. Block 61 of FIG. 6 illustrates the standard resting or time-of-day mode to which the microprocessor returns when no other function is being performed. In this mode, the liquid crystal display 2 displays the time of day and a flashing ":" to indicate that the monitor is operating. Blocks 62–68 illustrate the various user inputs which can be detected by the microprocessor. Blocks 62–67 correspond to the push buttons 9–14, respectively, which are illustrated in FIGS. 2, 3 and 4 on the top of the monitor housing. Blocks 68 and 69 correspond to the input received when a drawer is opened or when a scheduled time is reached, respectively.

Figure 11:
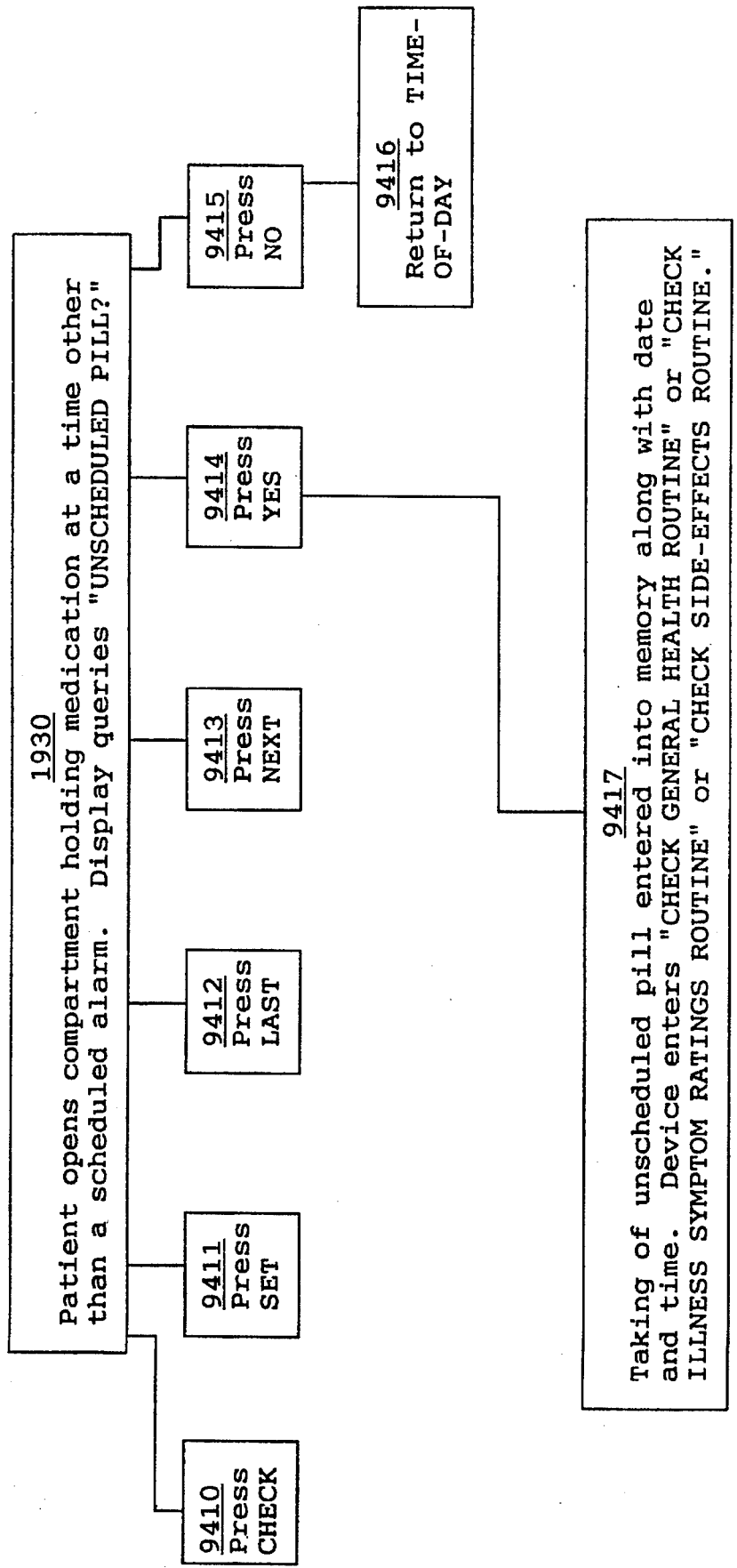
FIG. 11 is a flow chart of the UNSCHEDULED PILL routine.

If a drawer is opened while the microprocessor 1 is in this mode, as illustrated by block 68, the microprocessor will jump to the unscheduled pill routine designated by block 616 and further detailed in FIG. 11.

Figure 18:
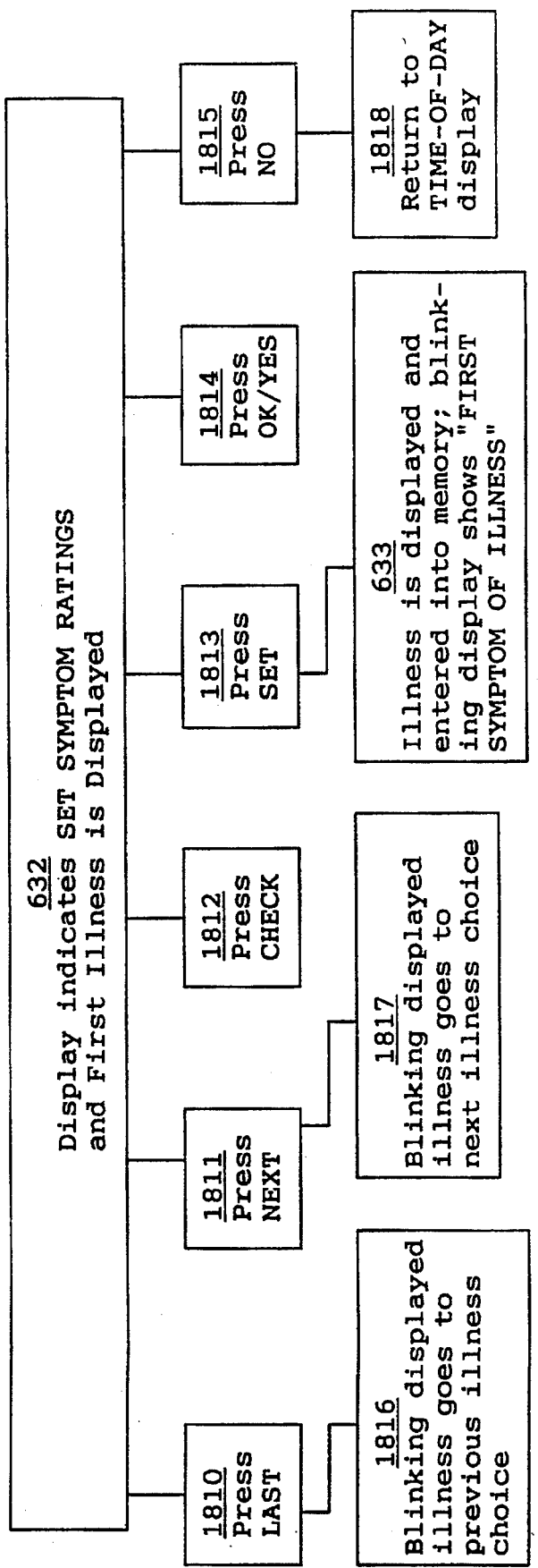
FIGS. 18 and 19 are flow diagrams of the CHECK ILLNESS SYMPTOM RATINGS routine.

If the patient intends to take an unscheduled pill, and presses the "YES" button, the microprocessor will jump to the Illness Symptoms Rating routine designated by block 632 and further detailed in FIG. 18. If desired, the microprocessor could also jump to the Check General Health routine designated by block 638 and further detailed in FIG. 23, after the routine in FIG. 18 is completed. The microprocessor could also jump to the Check Illness General Information and Drug Interactions routine designated by block 635 and further detailed in FIG. 21. The Check Warnings and Instructions routine designated by block 634 and further detailed in FIG. 20 could also be activated.

The unscheduled pill routine is entered through the enabling of one of the inputs connected to the drawer switch circuitry 8 as illustrated in FIG. 1. This occurs when a drawer is open and the corresponding switch is triggered without the user first being prompted by the occurrence of a scheduled medication alert through the running of the alarm routine.

Any of the above mentioned routines can also be activated by the patient at any time he or she selects, as shown in FIG. 6, beginning with the Block Diagram 61 by pressing the "CHECK" button, to access the particular routine desired. This allows the patient to cycle through first dose time, schedule 1, schedule 2, schedule 3, schedule 4, side-effects setting, illness symptom rating, warnings and instructions, and illness general information and drug interactions.

Figure 25:
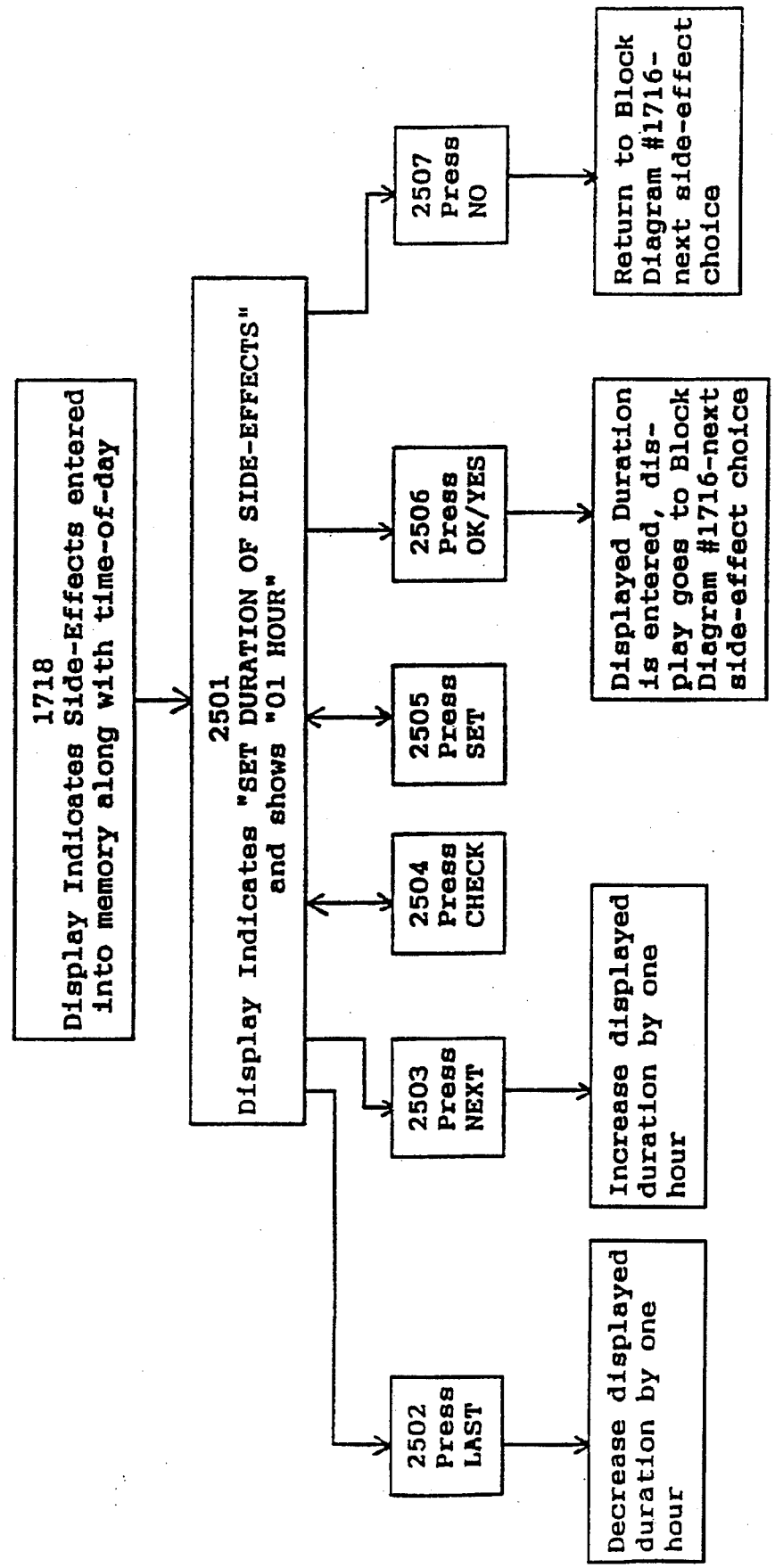
FIG. 25 is a flow chart of the SIDE-EFFECTS DURATION routine.
Figure 26:
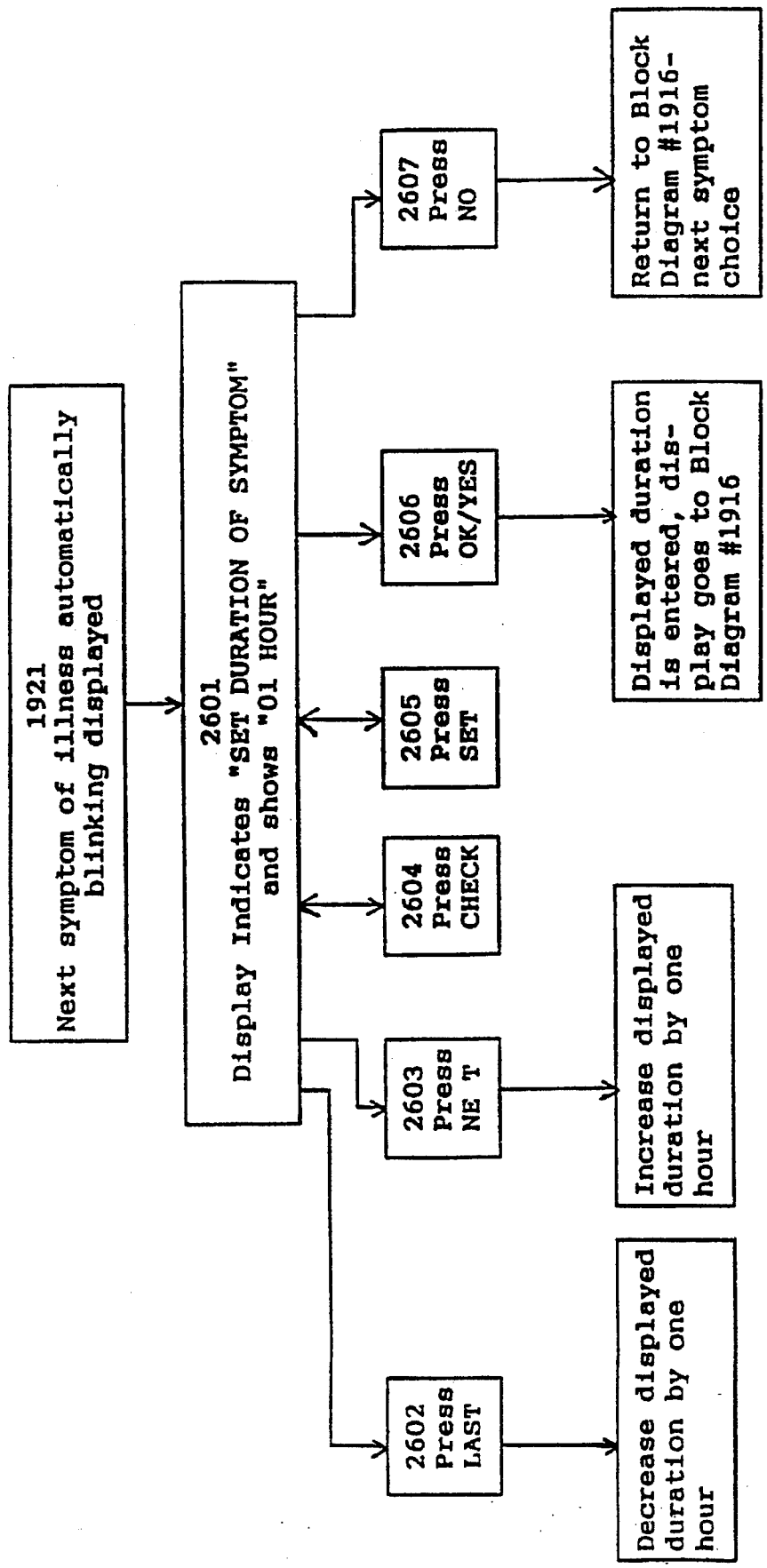
FIG. 26 is a flow chart of the SYMPTOMS DURATION routine.

In addition, each time the Illness Symptom Rating Routine is activated, the Symptom Duration Routine of Block Diagram 1921, further described in FIG. 26, can be activated. As well, each time the Side-Effects Setting Routine is activated, the Side-Effects Duration Routine can be used to record the duration of each side-effect, as shown in Block 1718, FIG. 25 (Page 23).

Actuating one of the user input buttons 9–14, will cause the microprocessor 1 to enter the appropriate corresponding routine. Actuating the "YES/OKAY" button 13, as illustrated by 66, and maintaining the button actuated for at least one second will cause the audible alarm to be reactivated if it has been suspended. Maintained actuation of the "NO" button, as illustrated by blocks 67 and 624, will cause the audible alarm to be deactivated. Actuation of the "set" button 12, as illustrated by block 65, will cause the microprocessor 1 to enter the time setting routine better illustrated in FIG. 10. Once the time setting routine has been competed, the microprocessor 1 will return to the time of day display mode as described above.

Figure 7:
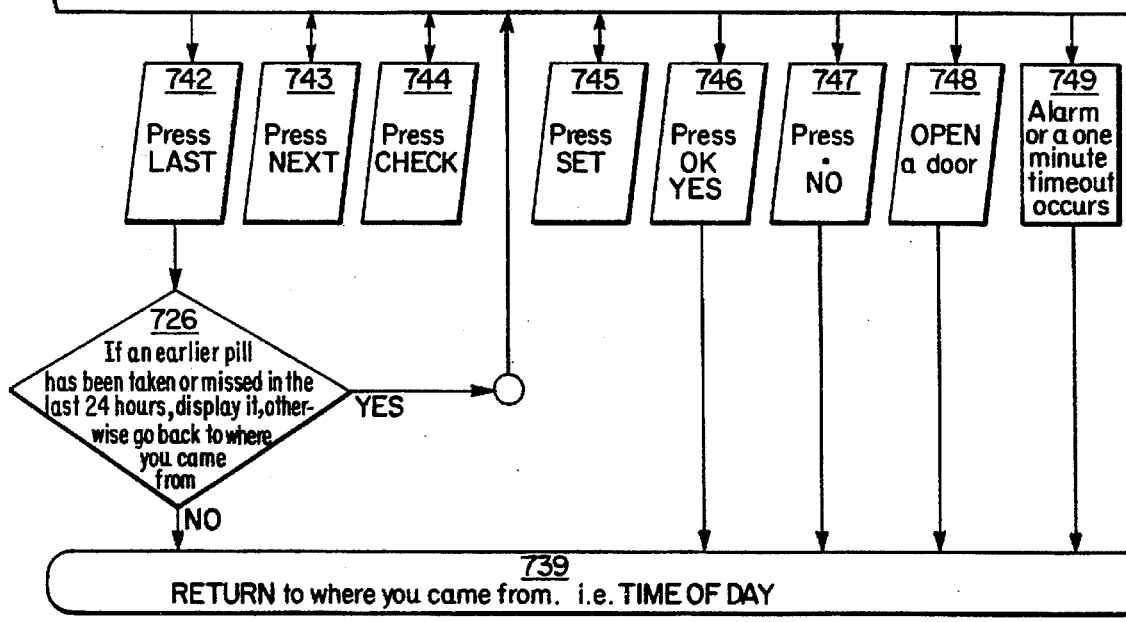
FIG. 7 is a flow chart showing the LAST routine.
Figure 8:
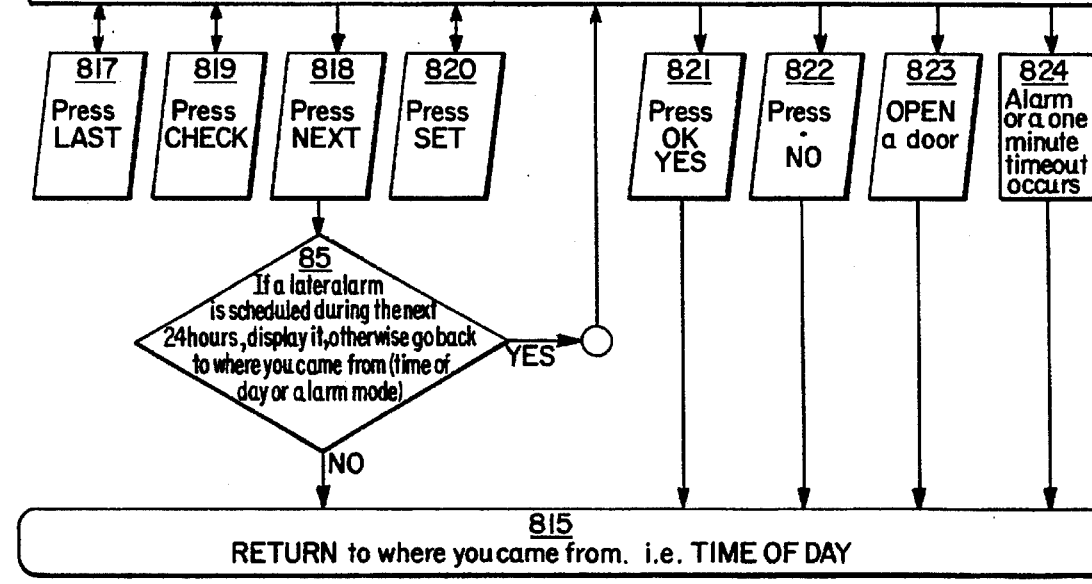
FIG. 8 is a flow chart of the NEXT routine.

Actuating the "LAST" button 9 or the "NEXT" button 10 will cause the microprocessor to display the last 24 hours of access to the drawers including; medication taken on schedule, missed medication, and unscheduled compartment openings; or the next 24 hours of scheduled medication, respectively, by entering the last routine, FIG. 7, or the next routine, FIG. 8, respectively.

Figure 9:
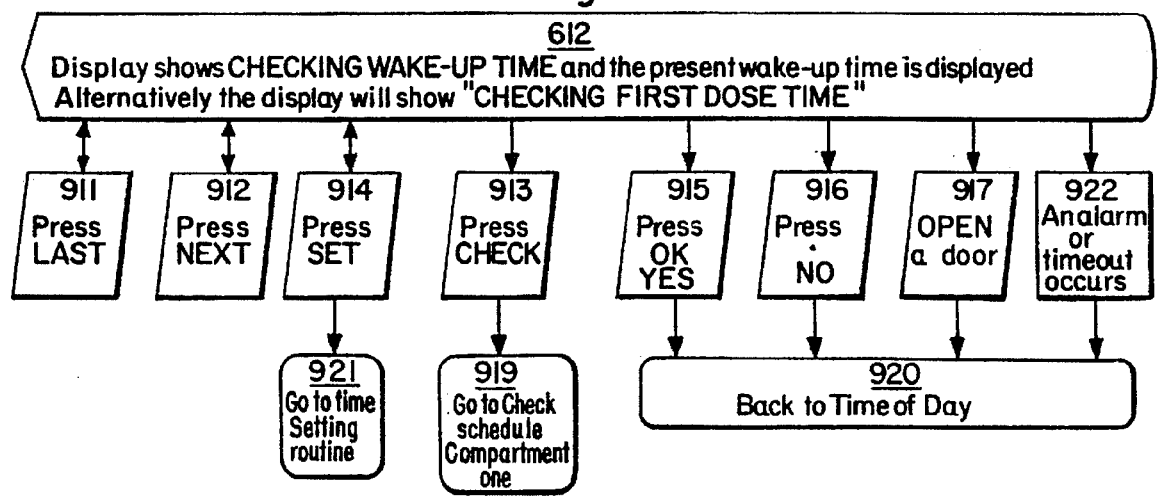
FIG. 9 is a flow chart of the WAKE-UP TIME CHECKING routine.

Actuation of the "CHECK" button 11 will cause the microprocessor 1 to go into the First-Dose-Time routine as illustrated by block 612 and in greater detail in FIG. 9. As illustrated in both FIGS. 6 and 9, the user can elect to go to the check schedule routine, block 618, or to return to the time of day display. The check schedule routine, illustrated in detail in FIG. 13, allows the user to check the scheduling stored in the microprocessor 1. It also enables the user to cycle through checking "BEEP VOLUME," "BEEP OFF" number of hours, and "TIME OF DAY". Actuation of the "Check Button" 11 also enables the user to cycle through clocking "Side Effects," "Illness Symptom Ratings," "Warnings and Instructions," "Illness General Information and Drug Interactions" and "General Health Check." The General Health Check Routine can also include questions regarding the patient's attitude and expectations regarding their illness, questions about their lifestyles and habits, and a routine or algorithm for self-diagnosis.

When in the "LAST" routine, as illustrated in FIG. 7, the display 2 initially indicated the most recent time that a compartment was opened, or a take medication alert was generated. The display also indicates the number of pills, and the compartment corresponding to the particular scheduled medication. If a medication signal was generated, and the appropriate compartment was not opened in a predetermined time period (e.g. 10 minutes or 1 hour), the LCD will also display a "missed pill" indication, corresponding to that scheduled medication alert. If a number of medication alerts or unscheduled openings of a drawer occurred simultaneously, each of the medication signals will be displayed sequentially, through sequential actuation of the "LAST" button 9, while the time indication of the time of each of these events remains the same.

Actuation of the "LAST" button 9 during this routine will continue to sequence through each of the last occurrences during the previous 24 hours, displaying each occurrence after each actuation of the "LAST" button 9, until the entire previous 24 hours of activity of the device has been replayed. Once the last full 24 hours has been displayed, (or a longer time period if additional memory has been added), actuation of the "LAST" button 9 will take the flow of the microprocessor 1 back to that location in its operation prior to the initial selection of the last routine, or return to "TIME-OF-DAY".

During the "LAST" routine, actuation of the "NEXT" button 10, the "CHECK" button 11 or the "SET" button 12 will have no effect on the operation of the microprocessor 1 or the display 2. Actuation of the "YES/OKAY" button 13 or the "NO" button 14 or the opening of one of the compartments or the occurrence of a medication alert time will cause the last routine to terminate and the microprocessor to return to that location in its operation prior to the initial selection of the last routine, or return to "Time-of-Day?".

FIG. 8 illustrates the "NEXT" routine, which is similar to the "LAST" routine above. In this mode, each designated medication time for each compartment, with each quantity of medication, over the next 24 hours is displayed through sequential actuation of the "NEXT" button 10. Once all of the scheduled times have been displayed for the next 24 hour period, the microprocessor 1 is sequenced back to that location in its operation prior to the initial selection of the next routine, or returned to "Time-of-Day?". The "LAST" 9, "CHECK" 11 and "SET" 12 buttons are rendered ineffective during the "NEXT" routine. Actuation of the "YES/OKAY" 13 or "NO" 14 button or the opening of one of the compartments or the occurrence of a medication alert time will cause the next routine to terminate and the microprocessor 1 to return to that location in its operation prior to the initial selection of the next routine, or return to "Time-of-Day?".

The provision of these two routines allows the user or other monitoring personnel to prospectively view the programmed medication times for the next 24 hour period and to retrospectively view the medication administered or missed during the last 24 hours. The device is therefore not limited only to medication reminding but also allows for medication monitoring. Through the extension of the internal RAM storage of the microprocessor 1, information covering a time period greater than 24 hours can be stored. An optional data port 33 can be provided to supply this prospective and/or retrospective information to an external device such as a printer, a data storage medium, a computer or other device.

Figure 10:
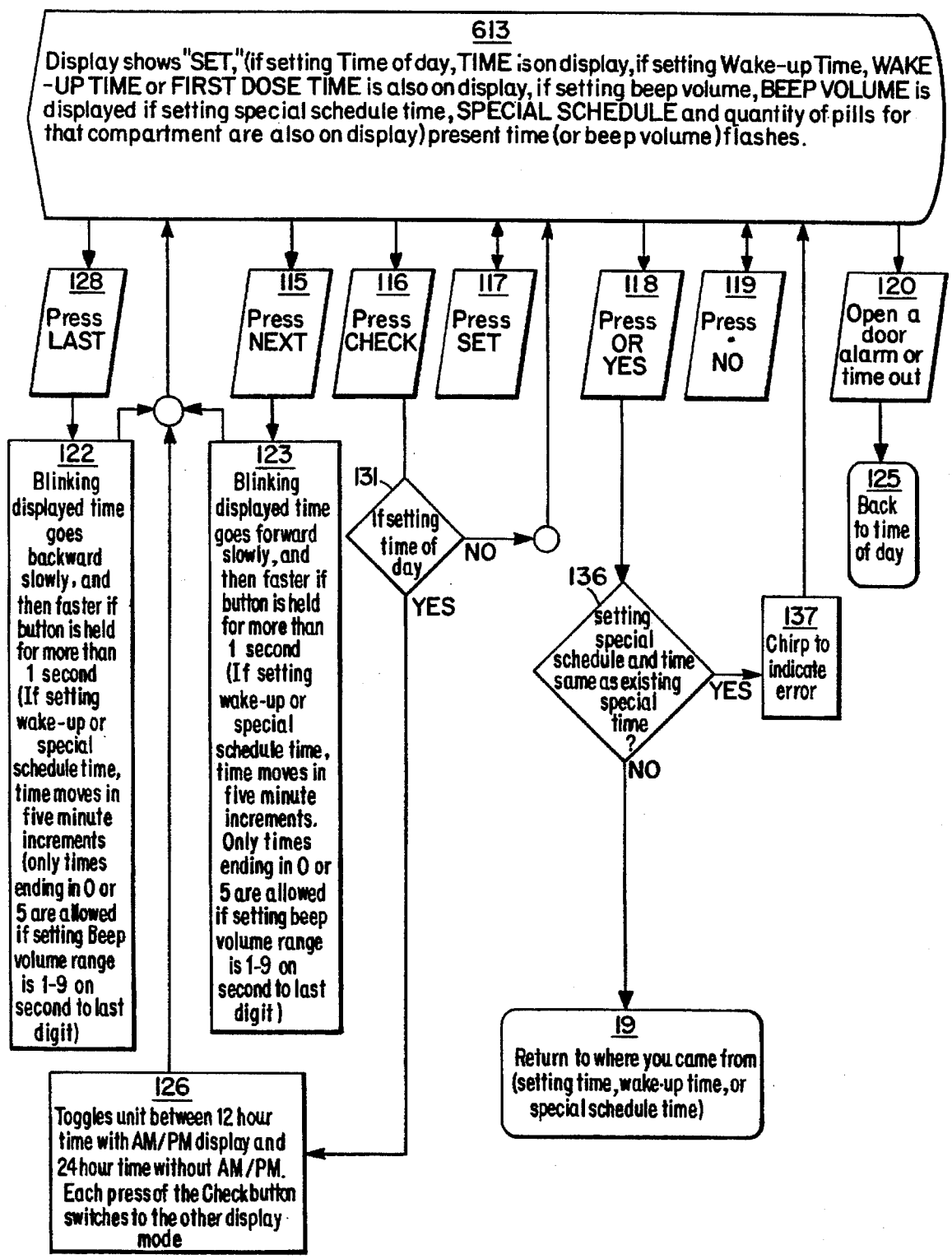
FIG. 10 is a flow chart of the TIME SETTING routine.

The check First-Dose-Time routine, FIG. 9, displays the preset First-Dose-Time and allows it to be changed by entering the time setting routine block 921, FIG. 10, by actuation of the "SET" button 12. From this routine, the medication alert schedule can also be viewed by actuation of the "CHECK" button 11. The Processor will then proceed with the check schedule routine, FIG. 13.

FIG. 10 illustrates the time setting operation of the microprocessor 1. This routine is used to set the time of day, to set the First Dose Time, and to set special scheduled medication times. Special schedule medication times are those which must be set at a particular time, for which the built in time increments such as "every-four-hours" will not provide. Therefore these times need to be specifically input. This routine is entered from each of these functions as appropriate to the performance of that function. When in the time setting routine, actuation of the "NEXT" button 10 increments the time and actuation of the "LAST" button decrements the time.

The unscheduled pill routine, FIG. 11, is entered when a drawer is opened at a time other then a scheduled medication time. This routine instructs the display 2 to display the appropriate quantity of pills for the drawer that was opened. The user is prompted via an audible "chirp" and the query "UNSCHEDULED PILL?" to indicate whether or not an unscheduled medication is being taken. If the user actuates the "YES/OKAY" button 13 the microprocessor 1 will record that an unscheduled medication was taken. If the user does not respond within a predetermined period of time, or if the user actuates the "NO" button 14, the microprocessor will assume that no medication was taken. Each incidence of unscheduled medication is recorded for later review and display as described above in the "NEXT" and "LAST" review routines.

Figure 12:
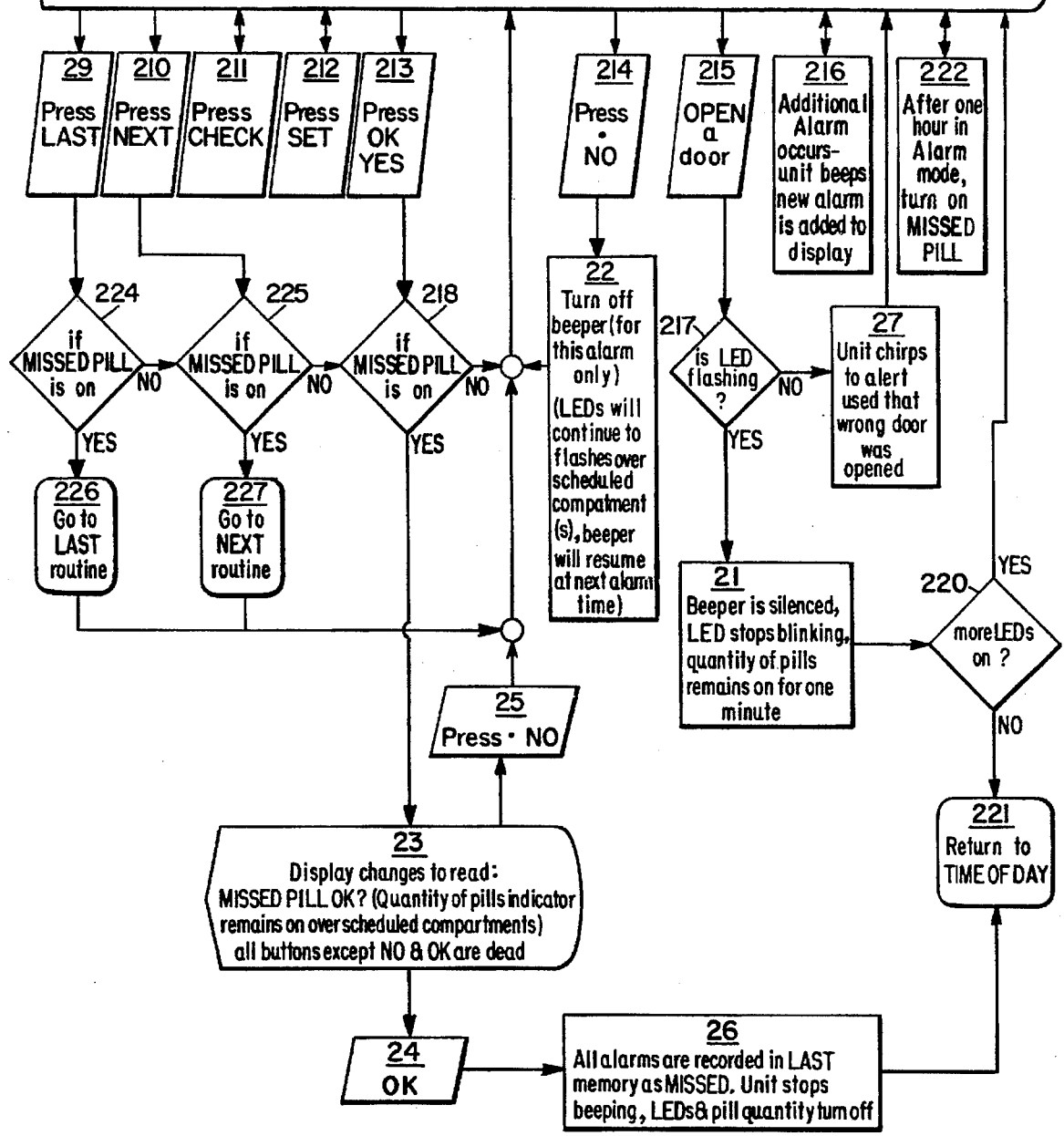
FIG. 12 is a flow chart of the ALARM routine.

The alarm mode block 617 of FIG. 12 is entered when the scheduled time and the time of day correspond. If the drawer of the compartment containing the correct pills is opened, the alarm condition is satisfied. If more than one compartment needs to be accessed, all compartments must be opened in order to satisfy the alarm condition. The user is prompted as to which drawers must be opened by the activation of the LED corresponding to the compartment and the indication of pill quantity above the compartment. If a wrong drawer is opened, the unit chirps and queries "UNSCHEDULED PILL?" to help prevent improper medication at an alarm time.

The user is also prompted if medication has been missed and can then view this missed medication through actuation of the "LAST" button 9 and can view the next medication by actuation of the "NEXT" button 10. The user can then decide to take the missed medication or not and so inform the microprocessor 1 by actuation of the "YES/OKAY" button 13 or "NO" button 14.

Figure 13:
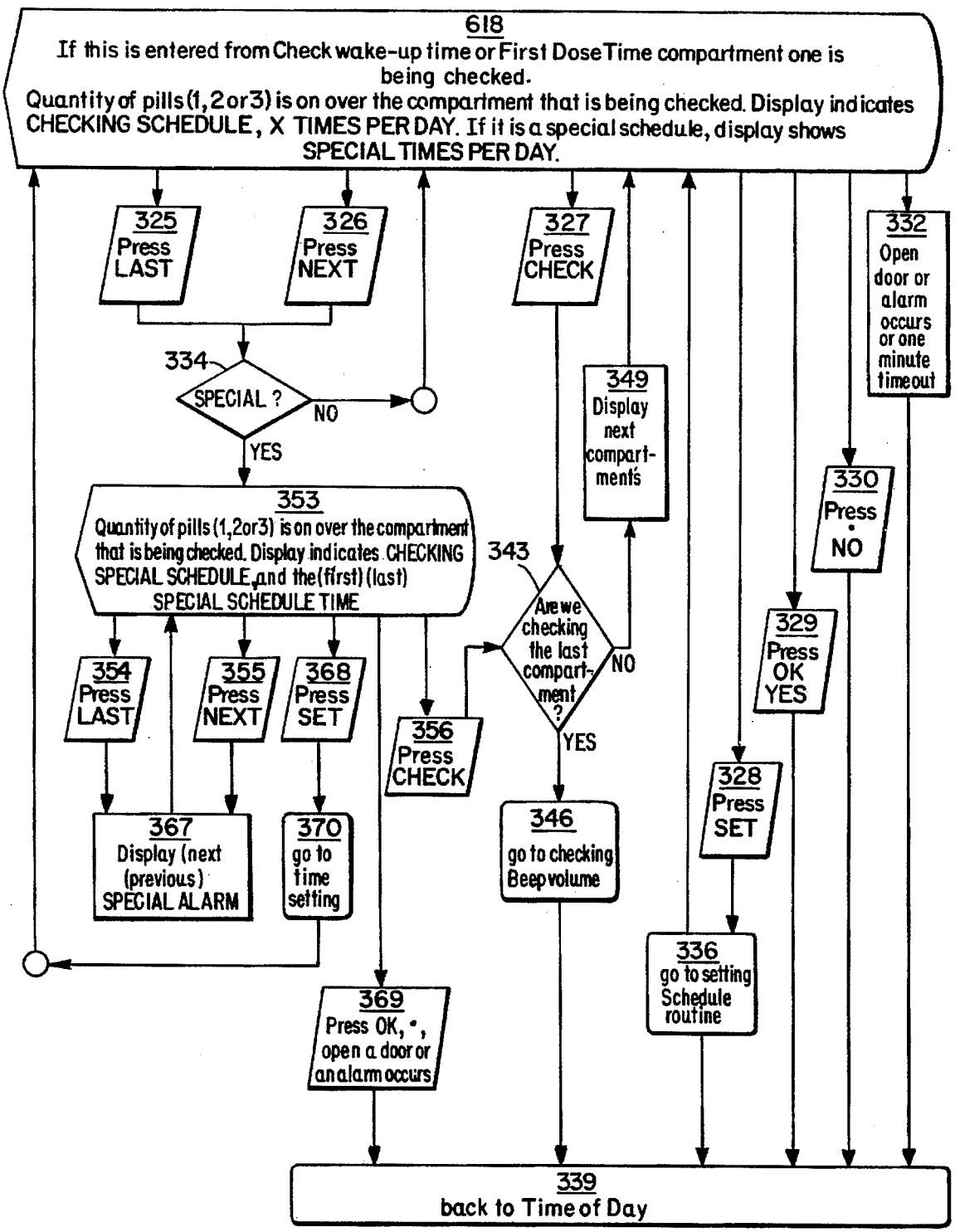
FIG. 13 is a flow chart of the CHECK SCHEDULE routine.

The check schedule routine FIG. 13 allows the user to sequentially view the schedule medication times by actuation of the "LAST" and "NEXT" keys. The time of medication is displayed, as well as the quantity and the LED of the appropriate compartment is activated.

Figure 14:
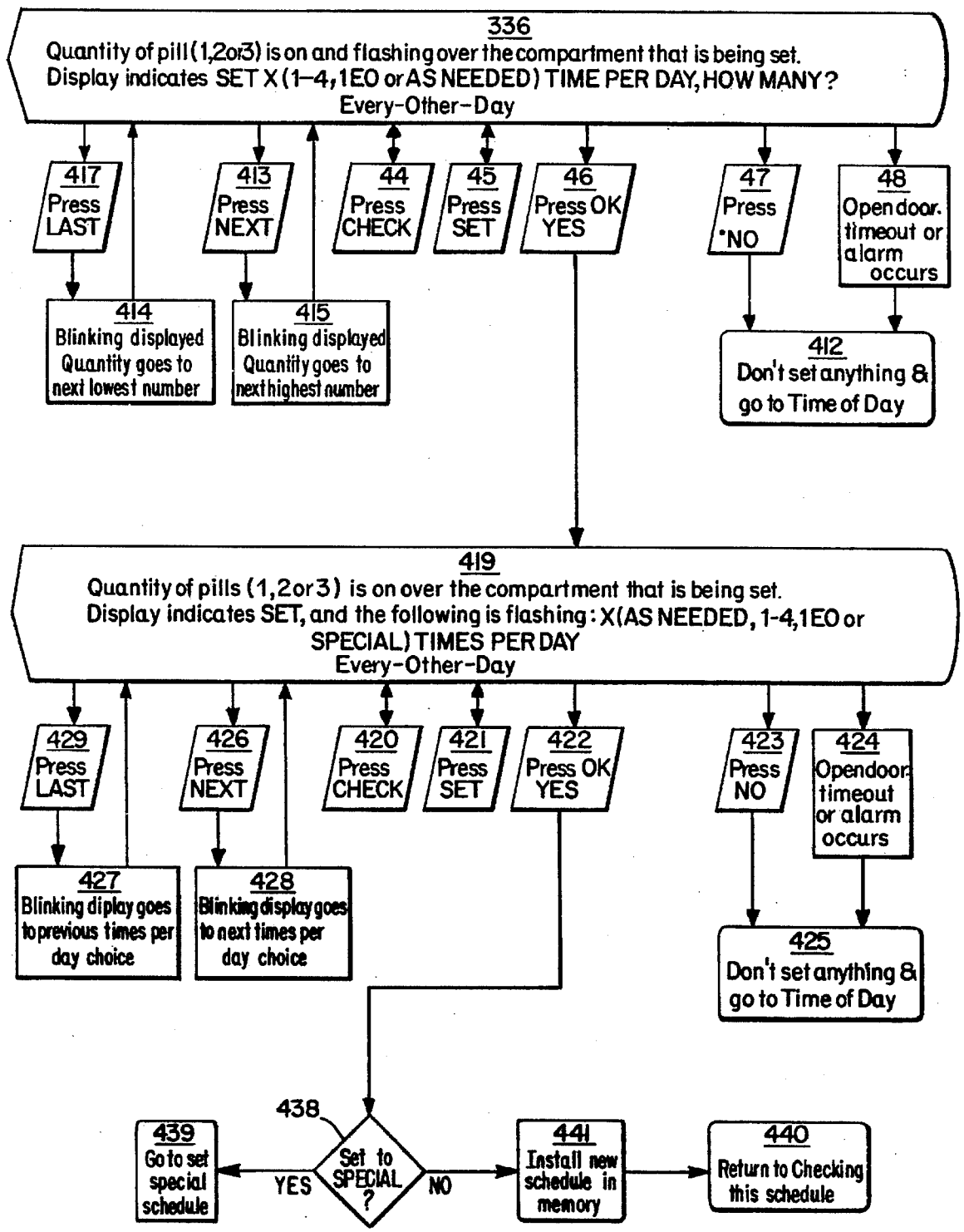
FIG. 14 is a flow diagram of the SET SCHEDULE: SET PILL QUANTITY and SET TIMES PER DAY routines.

FIG. 14 illustrates the logical operation of selecting the quantity of pills to be taken and selecting one of the preset, i.e. non-special, times per day settings for medication alerts.

Figure 15:
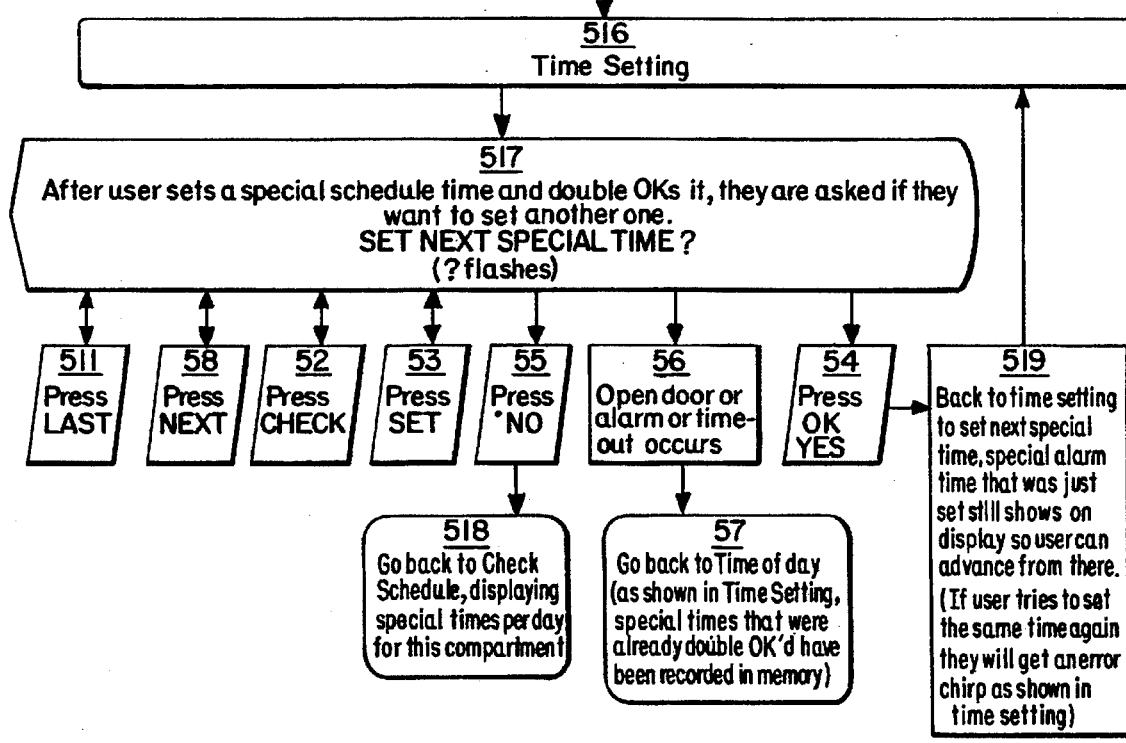
FIG. 15 is a flow chart for the SET SPECIAL SCHEDULE routine.
Figure 16:
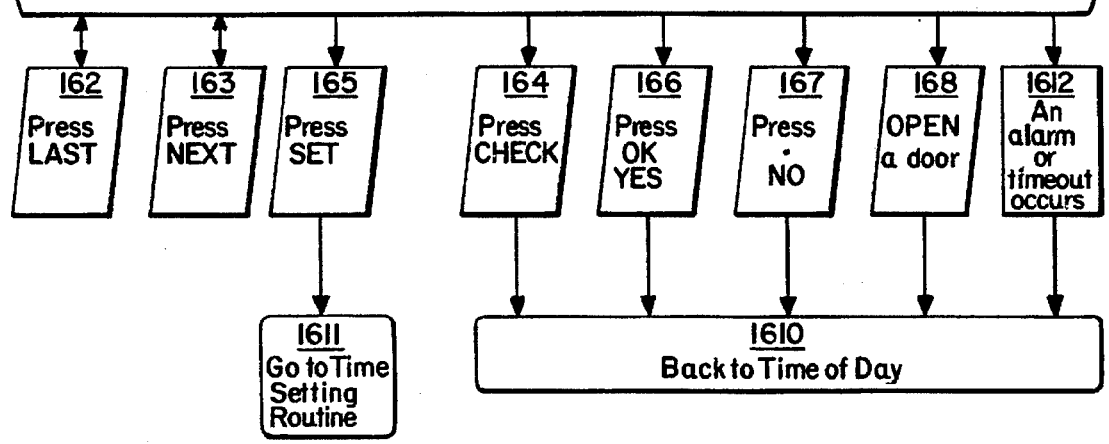
FIG. 16 is a flow chart for the CHECK BEEP VOLUME routine.

The set special schedule routine, FIG. 15 is a special case of the time setting routine, which, when entered allows the user to establish a non-standard medication alert time. Once this routine is entered, the patient or user can enter the specific times of day that medication should be taken allowing greater flexibility than simply choosing one of the present standards of "three-times-daily" etc.

If the patient intends to take an unscheduled pill, and presses the "YES" button, the microprocessor will jump to the Illness Symptoms Rating routine designated by block 632 and further detailed in FIG. 18. If desired, the microprocessor could also jump to the Check General Health routine designated by block 638 and further detailed in FIG. 23, after the routine in FIG. 18 is completed. The microprocessor could also jump to the Check Illness General Information and Drug Interactions routine designated by block 635 and further detailed in FIG. 21. The Check Warnings and Instructions routine designated by block 634 and further detailed in FIG. 20 could also be activated.

Figure 19:
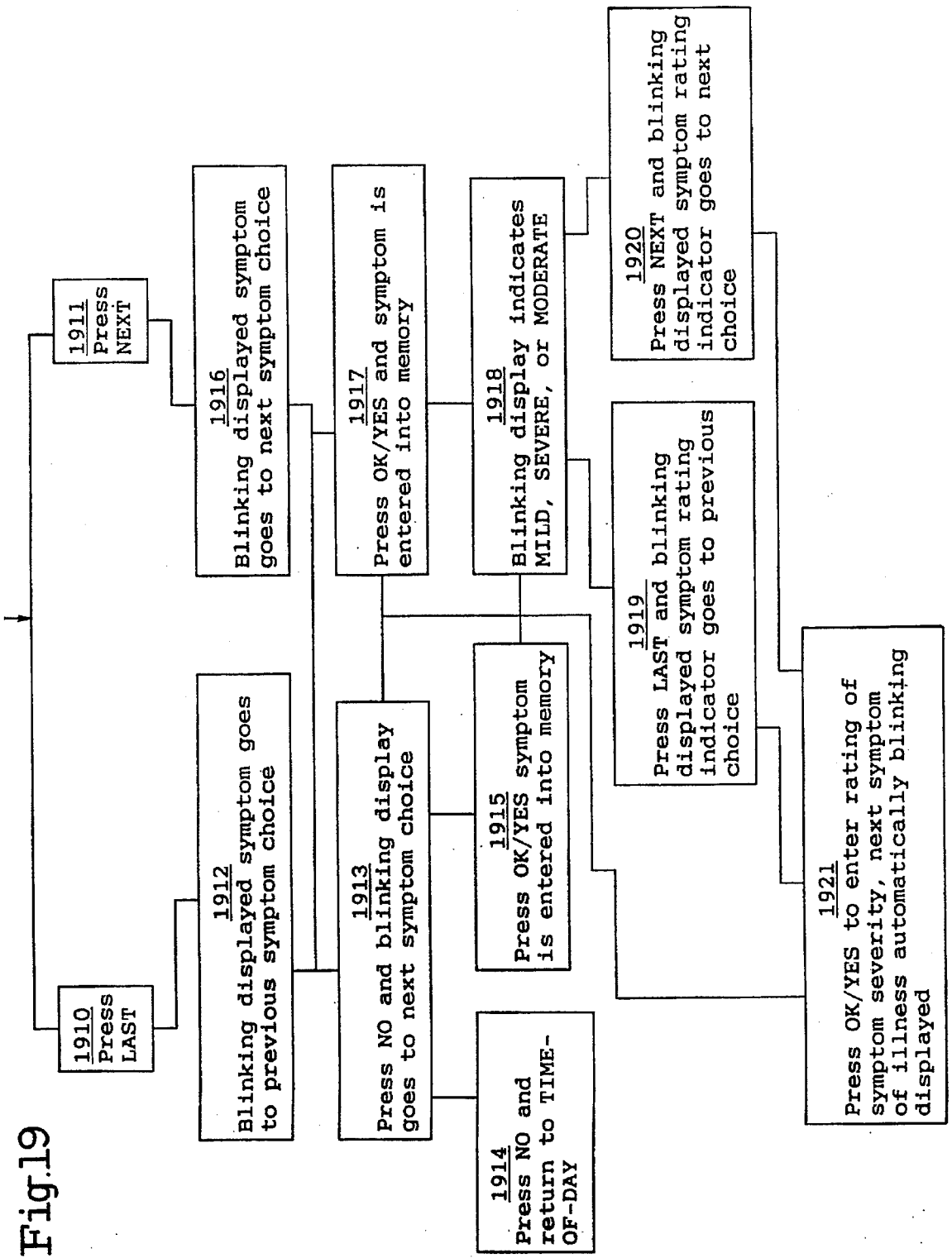

The FIG. 18 illustrates the logical operation of the "CHECK ILLNESS" routine. This allows the user to sequentially review the illnesses he or she is suffering from which are displayed on screen. For any particular illness display, the device can then display the symptoms commonly associated with that illness. The patient can then review these symptoms on screen, and enter a particular symptom that he or she is suffering from, and then rate the severity of that symptom as "mild," "moderate," or "severe." The routine works as follows: The user presses the "CHECK" button until the device displays "SET SYMPTOMS RATINGS" block 632. The user then presses the "NEXT" or "LAST" buttons and the illnesses that have been previously entered by the physician or pharmacist are sequentially displayed on the Bit-Map display 2. Once the display 2 shows the desired illness, the patient presses the "SET" button and that illness is entered into memory, and the display 2 shows that illness and the first symptom of that illness, Block 633. As shown in FIG. 19, the patient can then press the "NEXT" and "LAST" buttons sequentially to display each symptom of that illness that the patient may be experiencing. Once a symptom is displayed on screen 2 from which the patient is suffering, the patient presses the "OK" button and the symptom displayed is entered into memory. The patient then presses the "NEXT" and "LAST" buttons to sequentially display a severity rating such as "mild," "moderate," or "severe", Block 1918. When the appropriate rating of severity is displayed on screen 2, the user simply presses the "OK" button and that severity rating is entered for that particular symptom. After each symptom rating is entered, the device automatically displays the next symptom; see Block 1921 which allows the user to repeat the above sequence of button pushing until all the symptoms for that particular illness are entered and rated. At any time the patient can press the "NO" button and return to the next symptom on the list, Block 1913. Pressing "NO" again returns the device to "TIME-OF-DAY."

Through the use of a Bit-Map display 2 and a "HELP" routine, the patient could be given additional assistance in entering the particular side-effects or symptoms from which they are suffering. For example, after a particular side-effect is entered into memory, the display could query the patient, "ARE YOU HAVING OTHER SIDE EFFECTS? IF SO, PRESS 'NEXT' or 'LAST' TO DISPLAY THEM." The next side-effect would then be displayed on the screen 2 for review if the patient followed the instructions. Likewise, the patient can be queried regarding symptoms, to assist him or her in using the device. For example, when a particular illness is displayed, the device can query the patient, "IS THIS ILLNESS TROUBLING YOU TODAY?" If the user presses "OK" button, the device can then query "ARE YOU SUFFERING FROM THIS PARTICULAR SYMPTOM?" and list a particular symptom. If the patient answers "OK" the device could then query "IS THE SYMPTOM MILD?" and so on. If desired, the microprocessor could also jump to the Check General Health Routine designated by the block 638 and further detailed in FIG. 23, after the routine in FIG. 18 is completed.

Figure 23:
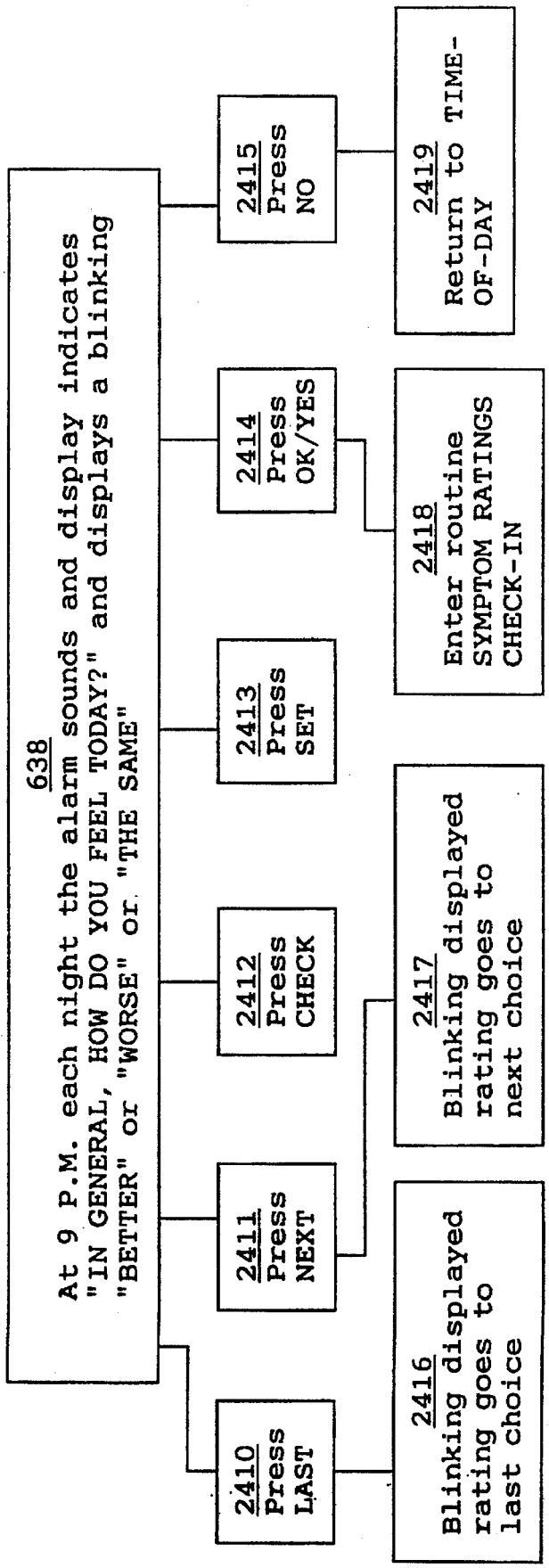
FIG. 23 is a flow chart of the CHECK GENERAL HEALTH routine.

FIG. 23 demonstrates the CHECK GENERAL HEALTH routine. This routine reminds the patient once-a-day to rate how they have been generally feeling, compared to previously. The patient answers "BETTER" or "WORSE" or "THE SAME" and therefore a running log of their subjective state of health is kept, to correlate with drug compliance, illness symptoms, side-effects, and drug dosage. As shown in Block 638 the alarm sounds at 9 p.m. (or any other time if so desired) and the display queries the patient "IN GENERAL, HOW DO YOU FEEL TODAY?" It displays a blinking "BETTER" or "WORSE" or "THE SAME." By using the "LAST" and "NEXT" buttons the patient can cycle through these three choices until the appropriate one is displayed. By pressing "OK/YES" the appropriate rating is entered into memory for the day. The display and software then automatically enter the SYMPTOM RATINGS CHECK-IN routine of FIG. 24, block diagram 637, to allow the patient to check in and rate the symptoms of his or her illness. The microprocessor could also jump to the Check Illness General Information and Drug Instructions routine designated by block 635 and further detailed in FIG. 21.

Figure 20:
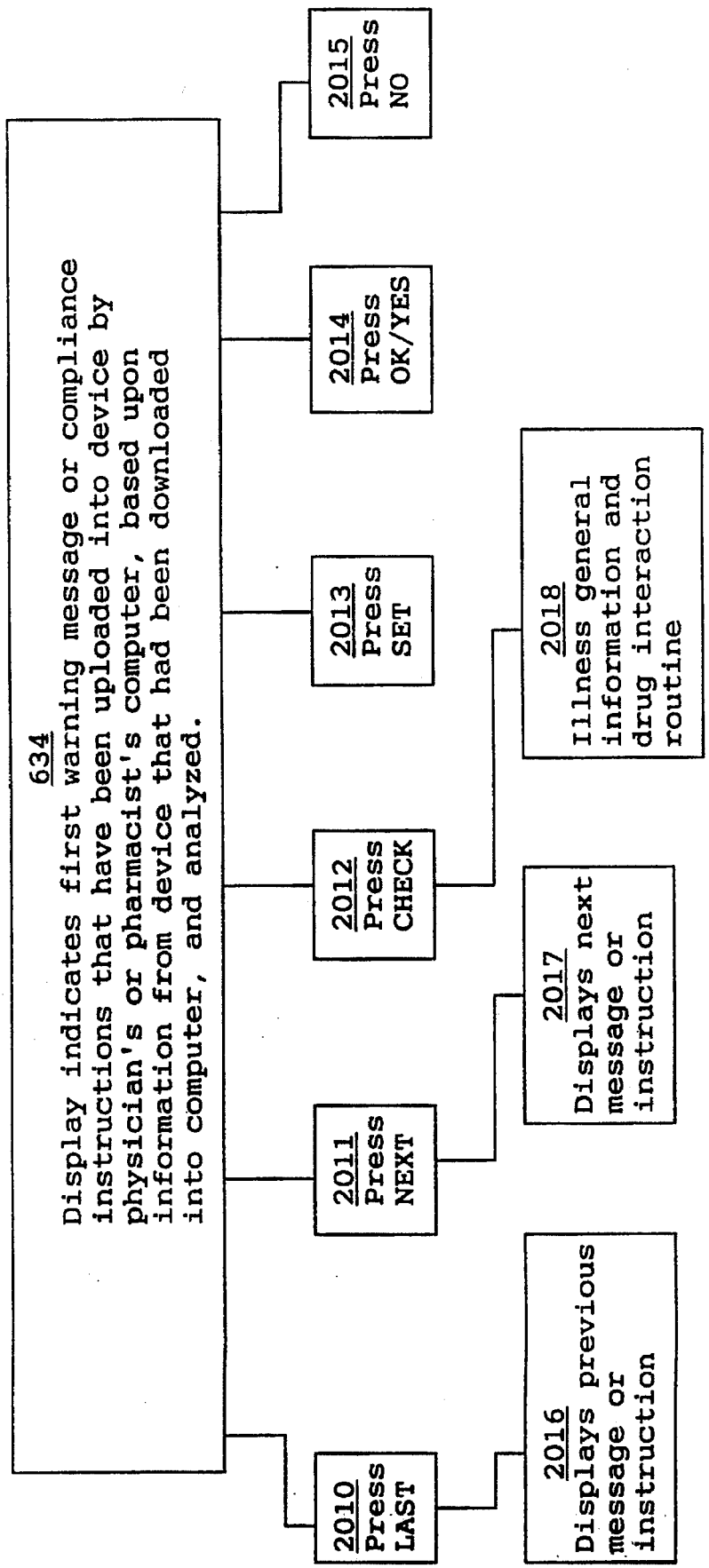
FIG. 20 is a flow chart of the CHECK WARNINGS AND INSTRUCTIONS routine.
Figure 21:
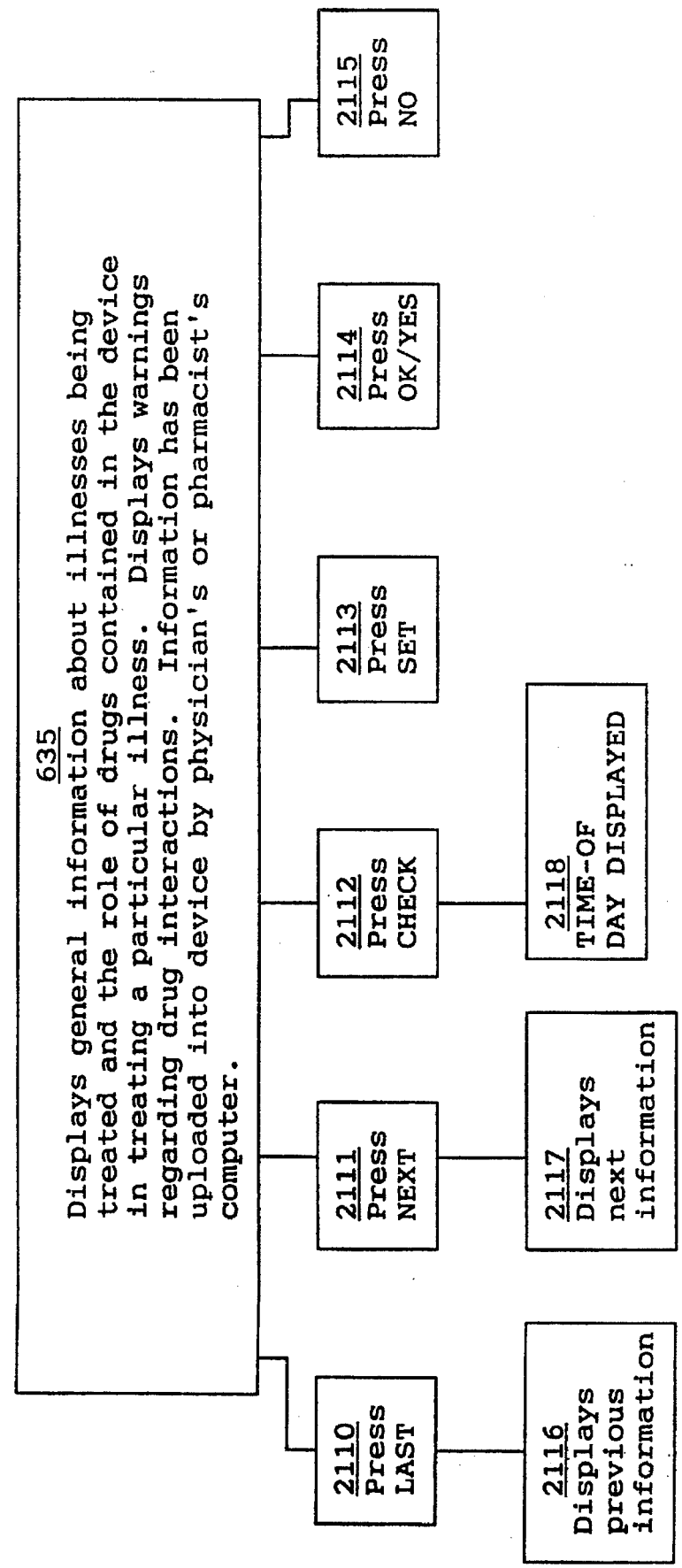
FIG. 21 is a flow diagram of the CHECK ILLNESS GENERAL INFORMATION AND DRUG INTERACTIONS routine.

FIG. 21 demonstrates how the patient displays information stored in the device related to the illnesses they have, and how the particular medications contained in the device are helpful in treating the illnesses. Information about potential drug interactions, or interactions with sunlight, food, etc., could also be displayed, as shown on Block 635. This information has been uploaded into the device by the physician's or pharmacist's computer based upon the drugs contained in the device. Pressing the "NEXT" or "LAST" buttons sequentially display the messages contained therein. Pressing the "CHECK" button returns the display to TIME-OF-DAY. The Check Warnings and Instructions routine designated by block 634 and further detailed in FIG. 20 could also be activated.

Figure 17:
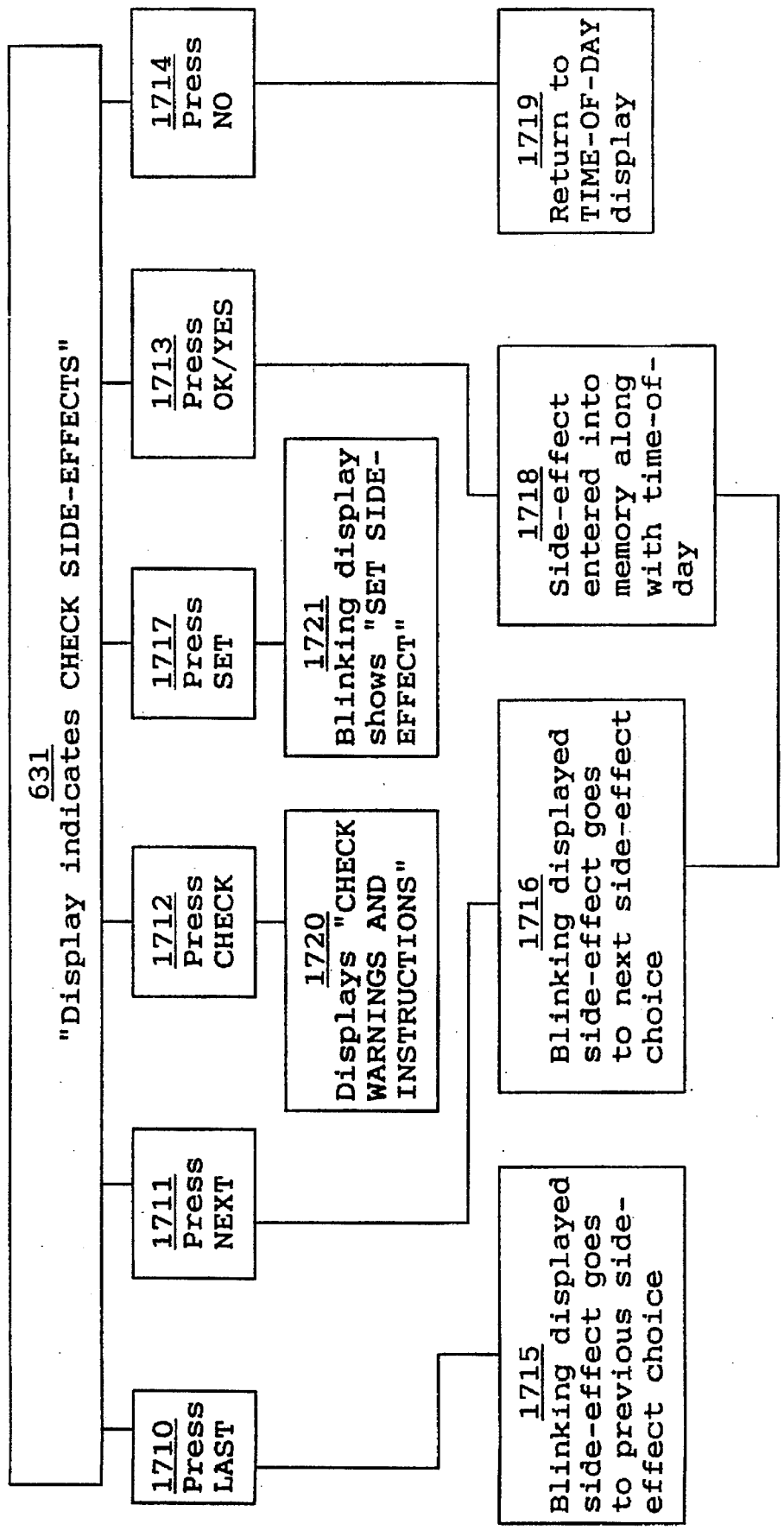
FIG. 17 is a flow chart for the SIDE-EFFECT SETTING routine.

The alarm routine may also cause the activation of the Illness Symptoms Rating Routine designated by block 632 and detailed in FIG. 18; the Check General Health Routine designated by block 638 and FIG. 23; the Check Illness General Information and Drug Instructions Routine designated by block 635 and further detailed in FIG. 21; and the Check Warnings and Instructions Routine of block 634 and FIG. 20; and the Side-Effects Setting Routine of block 631, FIG. 17.

Figure 22:
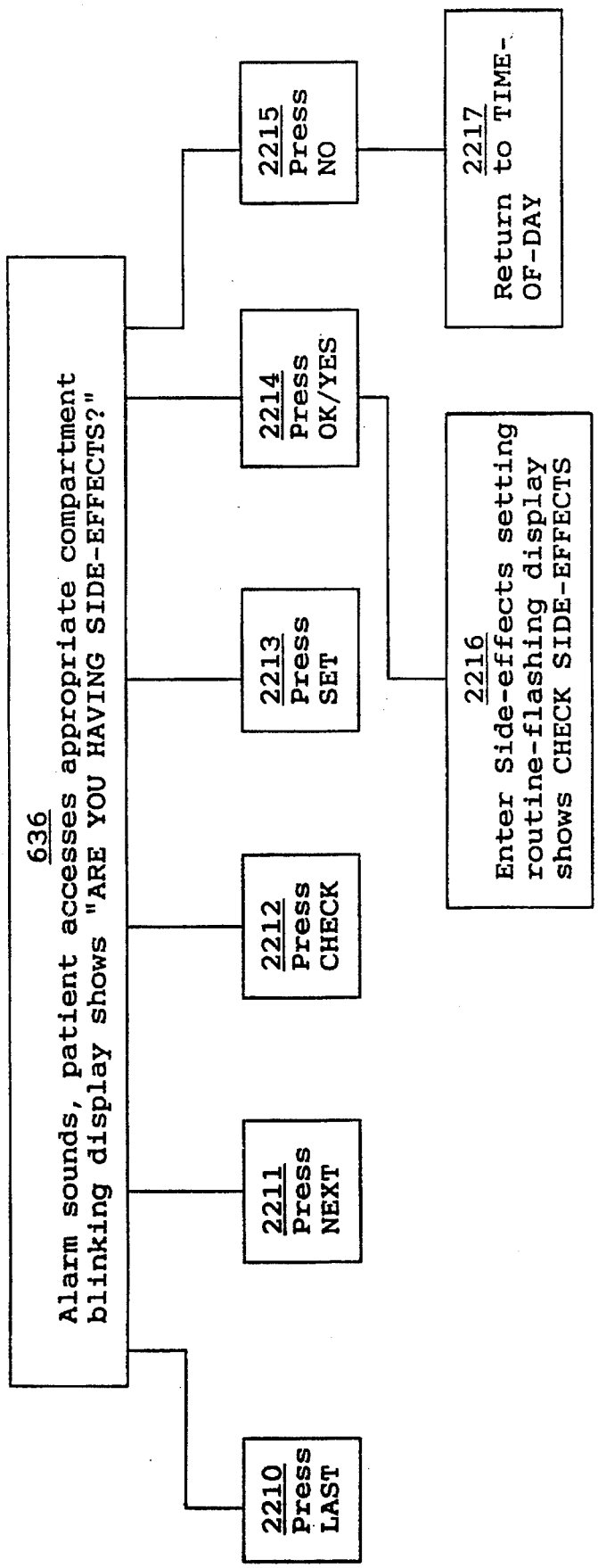
FIG. 22 is a flow chart of the ALARM BASED SIDE-EFFECTS CHECK routine.
Figure 24:
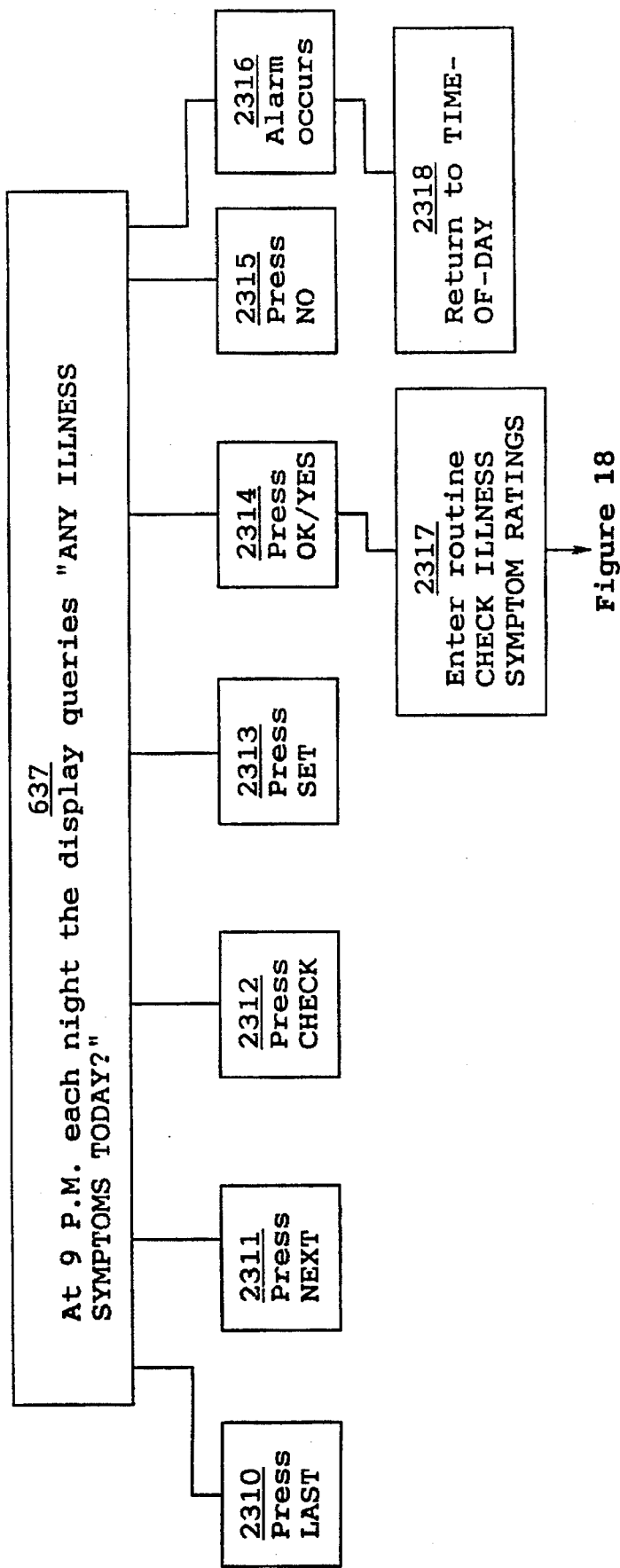
FIG. 24 is a flow chart of the SYMPTOM RATINGS CHECK-IN routine.

FIG. 24 demonstrates the SYMPTOM RATINGS CHECK-IN routine. This routine serves as a reminder to the patient, on a once-a-day basis, to enter the illness symptoms from which they've been suffering, and to rate them. This is important, as the patient may have forgotten to enter this information earlier in the day. Alternatively, the routine might be activated following each medication alert for medication prescribed for a specific illness. As shown in Block 637 of FIG. 24, at a selected time of day (demonstrated here as 9 p.m.). After the CHECK GENERAL HEALTH ROUTINE, the display queries "ANY ILLNESS SYMPTOMS TODAY?" By pressing the "OK/YES" button 13, the device enters the "CHECK ILLNESS SYMPTOM RATINGS" routine of FIG. 18, Block diagram 632. By pressing the "No" button 14, the device returns to TIME-OF-DAY. Should a medication alert signal also sound at the time of the Symptom Ratings Check-In routine, it must first be addressed as per FIG. 12, Block diagram 617. Then the ALARM-BASED SIDE-EFFECTS CHECK routine occurs as per FIG. 22, Block 636, and then the Symptoms Ratings Check-In routine will occur.

Likewise, the pharmaceutical manufacturer, physician or pharmacist might wish to know how long a duration the patient sustained a particular symptom or side-effect. This could work as follows: FIG. 17 demonstrates the "SIDE-EFFECT SETTING ROUTINE." In block diagram 1718 the side-effect is entered into memory along with the time of day. This routine could then branch into block diagram 2501 of FIG. 25 displaying the following message on the display "Set Duration of SIDE-EFFECTS 01 HOURS." By pressing the "NEXT" button, the number in the blank could be increased. By pressing the "OK/YES" button the correct number of hours for the particular side-effect would then be entered, and the routine would go on to block diagram 1716. Likewise, FIG. 19 can be modified in a similar fashion to FIG. 17 such that when the patient presses the "OK/YES" button, as noted in block diagram 1921, the device can then go on to the routine that allows the patient to set the duration of the particular illness symptom. This is shown in block diagram 2601, FIG. 26. The display indicates "Set Duration of Symptom –01 Hour". Pressing "NEXT" or LAST" displays the number of hours, and pressing "YES" enters the number of hours.

It is desirable to be able to plug certain software modules into the medication dispensing device. These modules could relate to specific diseases. For example, a module regarding heart disease could be plugged-in, that would give the patient information about heart disease, the medications used to manage it, and why particular types of medications are important to take. Any other disease could be incorporated into a particular module, which, when plugged into the dispenser could be activated to give patients information about the particular disease.

In addition, there could be modules specific for specific medications. These modules could give information about the medication, give side-effects about the medication, or give drug interactions that the medication has with other drugs.

By incorporating these disease-specific or drug-specific modules into the medication dispenser, the patient would be able to visualize, on-screen, information about the drugs, or diseases at selected times during the day, or during the particular delivery cycle of the drug. For example, when it was time for the alarm to sound to tell the patient to take the heart medication, the display could indicate to the patient that they were taking medication for the heart, what the underlying disease of the heart was, and why the medication was important to take.

Likewise, during selected times of the drug delivery cycle, the device could signal the patient, and the software containing information about drug side-effects would enable the display on-screen of side-effects specific for a particular drug. The patient could then rate these side-effects through the previously disclosed "SIDE-EFFECTS RATING ROUTINE."

Likewise, the disease-specific software would enable bringing on-screen all the specific symptoms of the illness, at selected times, which the patient could then rate according to the previously disclosed "ILLNESS SYMPTOM RATING ROUTINE."

An additional software module could be added that includes various drug interactions possibilities for the particular drugs that the patient is taking. At selected times throughout the drug cycle, the software package could enable a display on-screen questions regarding whether particular adverse reactions or drug interactions are taking place between the drugs. The patient could then answer yes or no as to whether these interactions are taking place, and could rate them according to the methodology previously described for rating "SIDE-EFFECTS SEVERITY." In this way pharmaceutical manufacturers could have more accurate information regarding adverse reactions and drug interactions, than they would have by just relying upon the patient's memory. This is because the device would enable the collection and correlation of information regarding when particular drugs of a multiple drug regimen are being taken, and when the particular adverse reactions or interactions take place.

These software modules could supplement or take the place of the uploading of information from the personal computer to the medication dispenser. Through plugging-in the software modules, it might then be unnecessary to upload data from the PC of the physician or pharmacist. Conversely, the software modules could be used in an intergrated fashion with the PC of the physician or pharmacist, as follows: the software modules provide disease-specific information regarding symptoms, and drug-specific information regarding side-effects and interactions, all of which the patient has entered and rated. This data could be downloaded into the PC, which could in turn upload certain messages to the patient about how to better manage the illness, medication, side-effects, or adverse reactions. Likewise, the PC could periodically update the software modules with new information about the drugs being taken, adverse reactions or side-effects.

Additional software modules can be developed to provide for information displayed to the patient, and data recorded by the patient. For example, the patient's underlying attitude toward their illness, and expectations of recovery or decline, could be assessed by a psychological instrument questionnaire provided by a software module. The questionnaire could assess optimism vs. pessimism, confidence in the drug regimen, confidence in the doctor, confidence in non-drug therapies, etc.

Another software module can be used to assess the patient's lifestyle and habits, to enable examiners to correlate these with the outcome of treatment. The software could display questions regarding, smoking, drinking alcohol, exercise, diet, job stress, work habits, etc.

By combining this data recorded with the previously mentioned data, a more complete picture of the factors that impinge on disease management, and the outcome of pharmacologic treatment, can be developed. This method of assessment will provide for a much more accurate assessment of the effects of drugs and other variables on disease progression and outcomes.

It may also be desirable to activate any or all of the above mentioned routines at various times throughout the medication taking cycle. The alarm routine could also be programmed to signal the patient to enter the above mentioned routines at the following times: peak dose time, when the drug is at its highest level in the blood; trough dose time, when the drug is at its lowest level in the blood; any pre-selected alarm time; and at the beginning or end-of-the day.

At any given date and time that data is entered into the monitor, the date and time of entry are recorded into the memory as well.

By then being able to display all the data entered, along with date and time, this data can be correlated with the medication compliance data displayed, and the effects of the medication taken or medication missed can be correlated with the other clinical information. All this data can be analyzed by the monitor itself, or downloaded as well into a computer for analysis, or printed to be made part of the medical record.

The realtime entry of this data, along with compliance data, does not therefore rely upon the memory of the patient to give compliance information, and other clinical information.

Figure 2B:
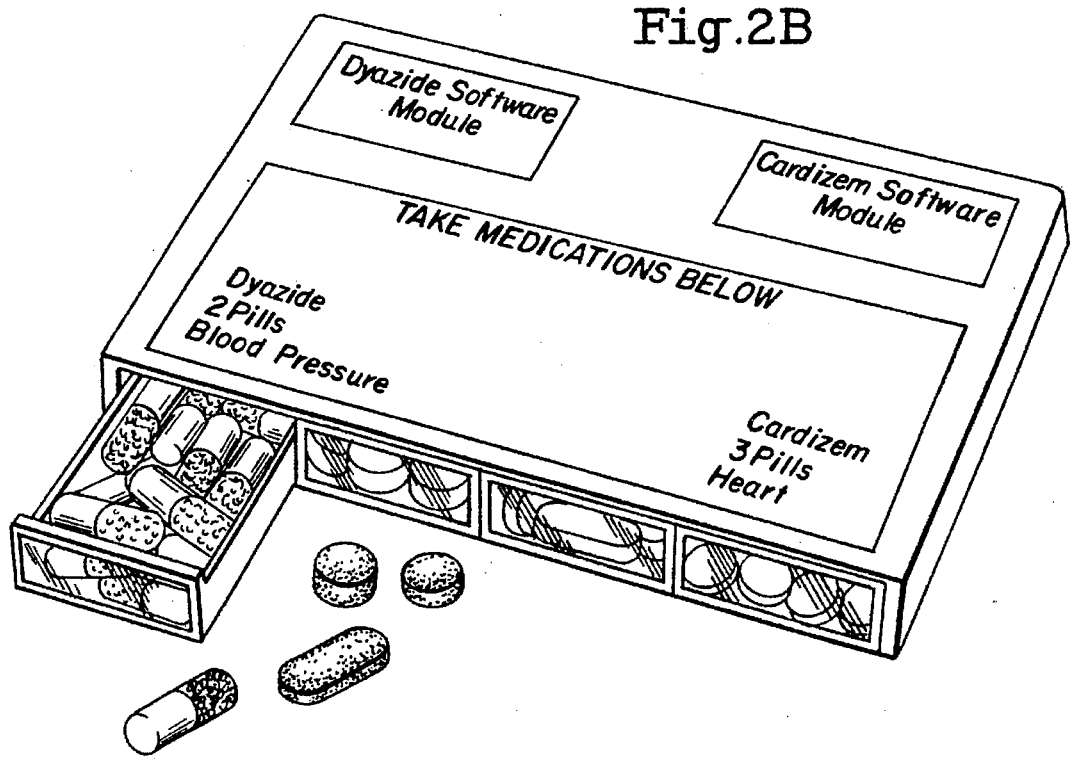
Figure 2C:
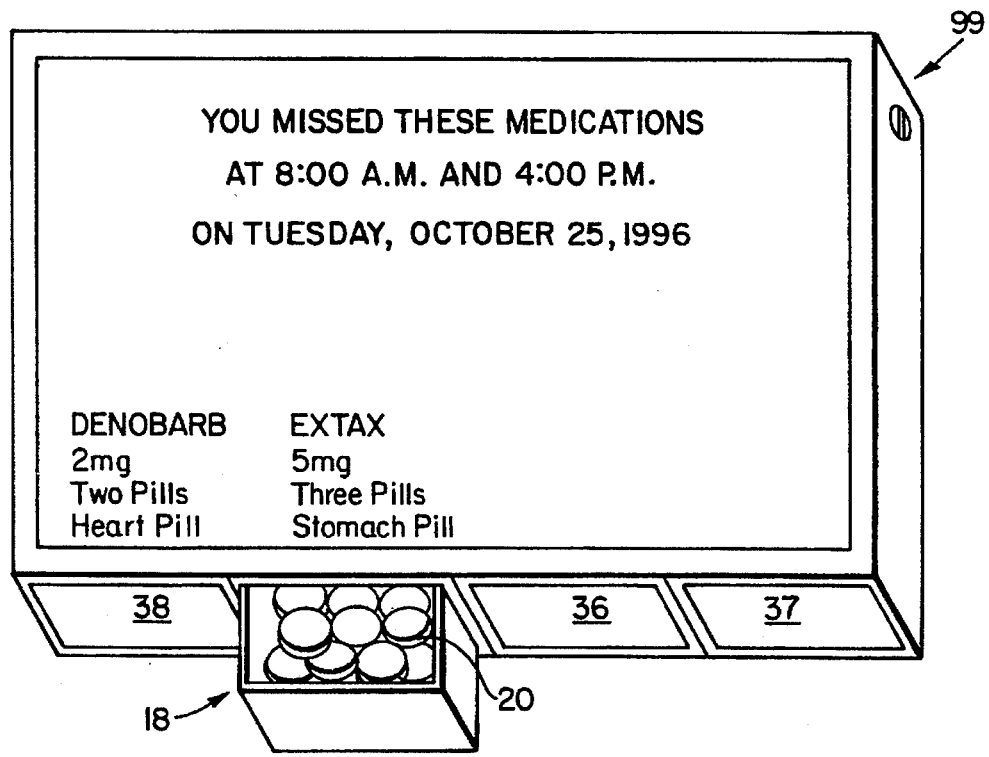
Figure 2D:
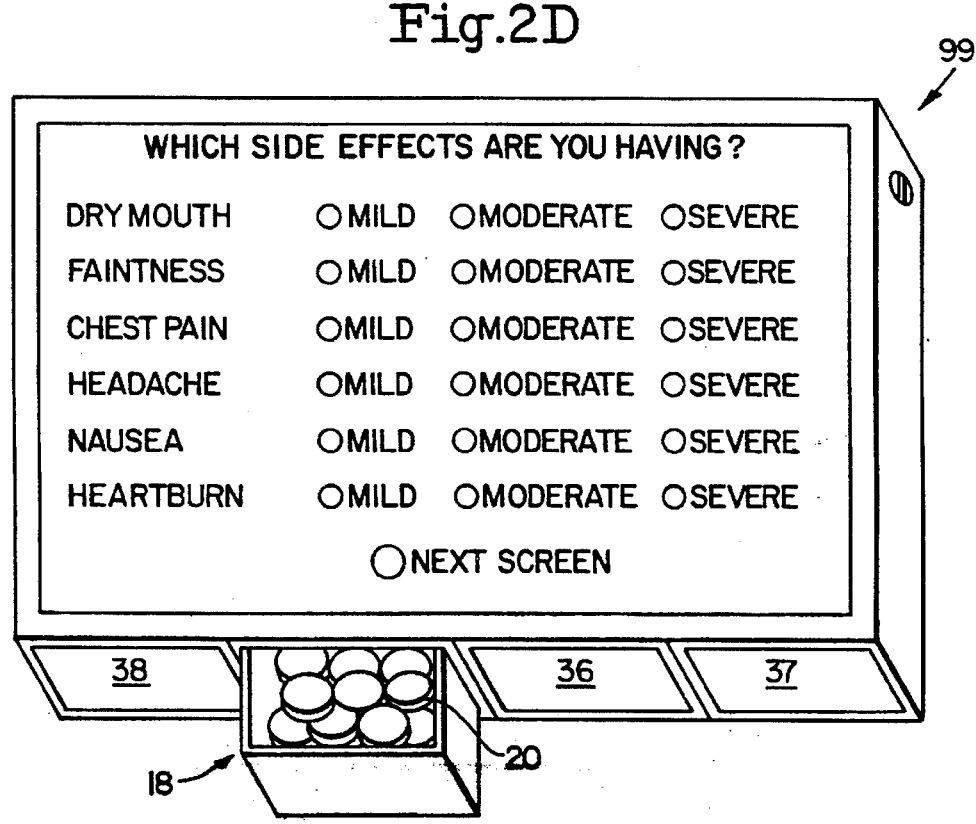
Figure 2E:
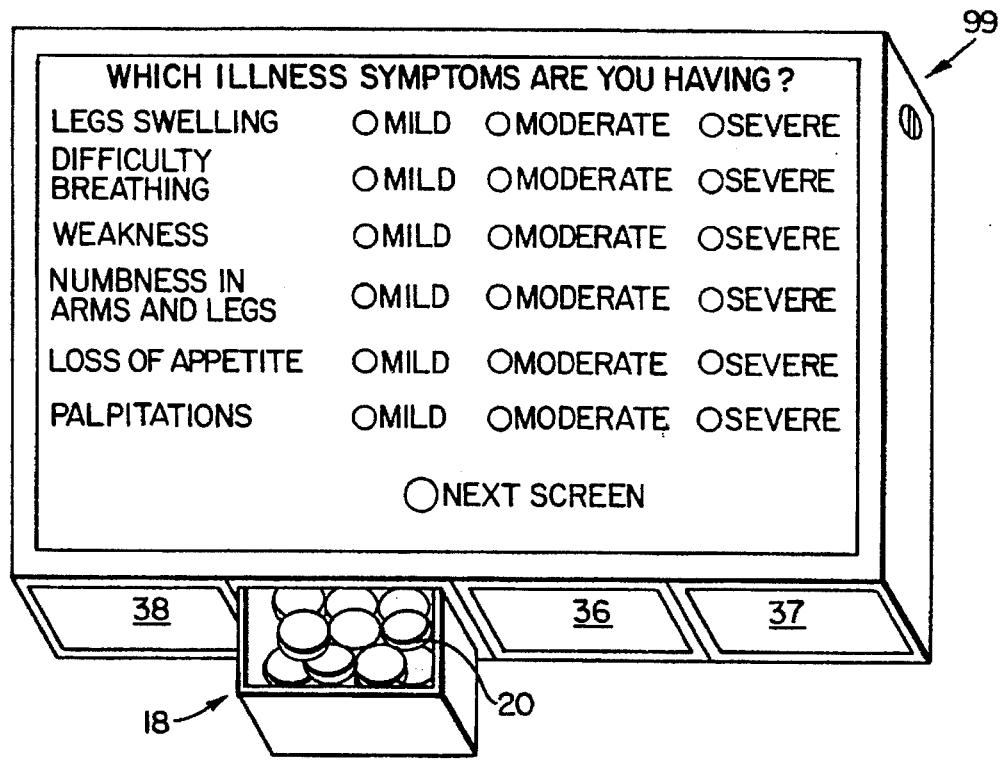
Figure 2F:
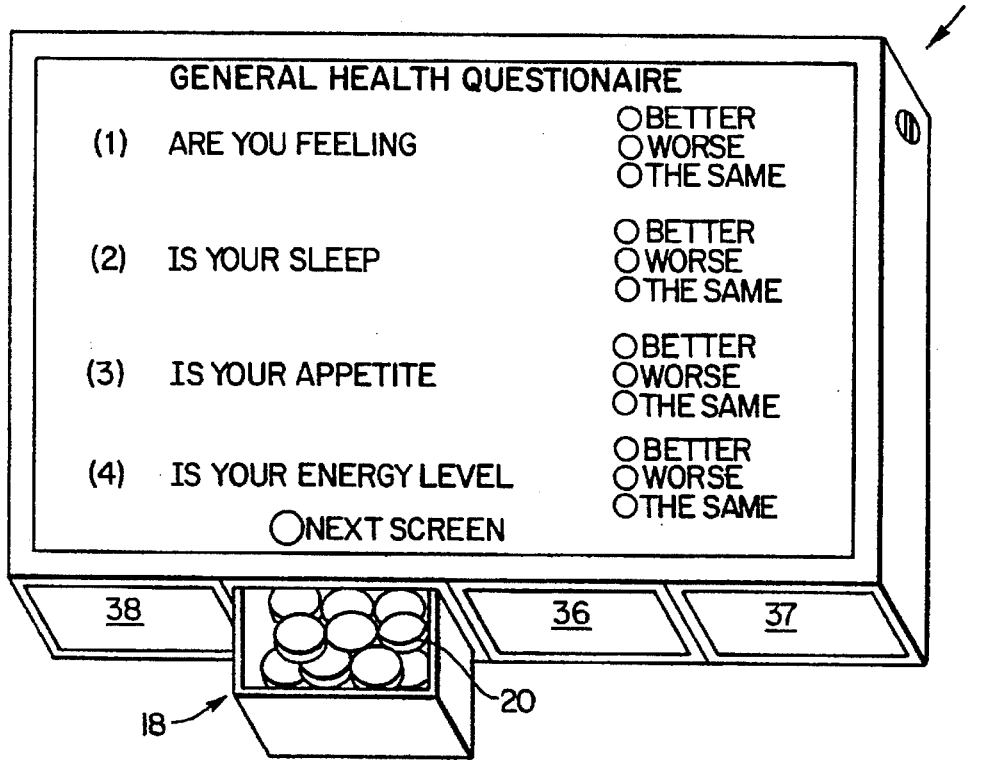

It is desirable to have a particular type of display on the device that will accommodate means of data entry that are easy for the patient to understand and use. Such a display 282 might include a "programmable touch screen display." Such a display is a form of a liquid crystal display, or "pixel display," and has the advantage of being programmable. The display has a number of "touch points" that can serve as capacitance based push buttons such as 281 of FIG. 2F. The display is programmed so that language appears on it, and the language is displayed along with a display of one or more buttons, that the patient can push. The programming of the display determines what language is displayed on the screen, and which portion of the screen shall serve as push buttons. The advantage of this technology for the medication dispenser is as follows: the display can be programmed to give the patient a series of questions to answer, and based upon which "button" on the display the patient presses, to answer the question, the display then displays the next message; in this way, sequentially, the display can lead the patient through a variety of messages, questions, and prompts which will be altered sequentially, based upon the patient's pushing of a particular button on the preceding message displayed; in addition, the display can show certain pictures, for example, if the patient misses a medication that is important for a patient who is epileptic, so that they don't have a seizure, the display could show a human figure falling down on the ground as a sign of the importance of taking the medications; in addition, this type of display lends itself to presenting a questionnaire that the patient would answer regarding the type of side-effects and symptoms they are suffering from, and the severity of each; as shown in FIGS. 2D and 2E, respectively. It can also provide for a General Health Questionnaire, as shown in FIG. 2F, and display a record of medication taken and missed, as shown in FIG. 2C. Finally, this type of display can serve a "labeling function" by being able to label next to a particular medication cartridge, the type of medication contained in that cartridge, what the medication is for, and how many need to be taken, and such a display can flash and point an arrow at the particular cartridge indicated at the time the device gives an alarm signal, as shown in FIG. 2B. A self-diagnosis routine can be displayed and answered as shown in FIG. 31.

Figure 2G:
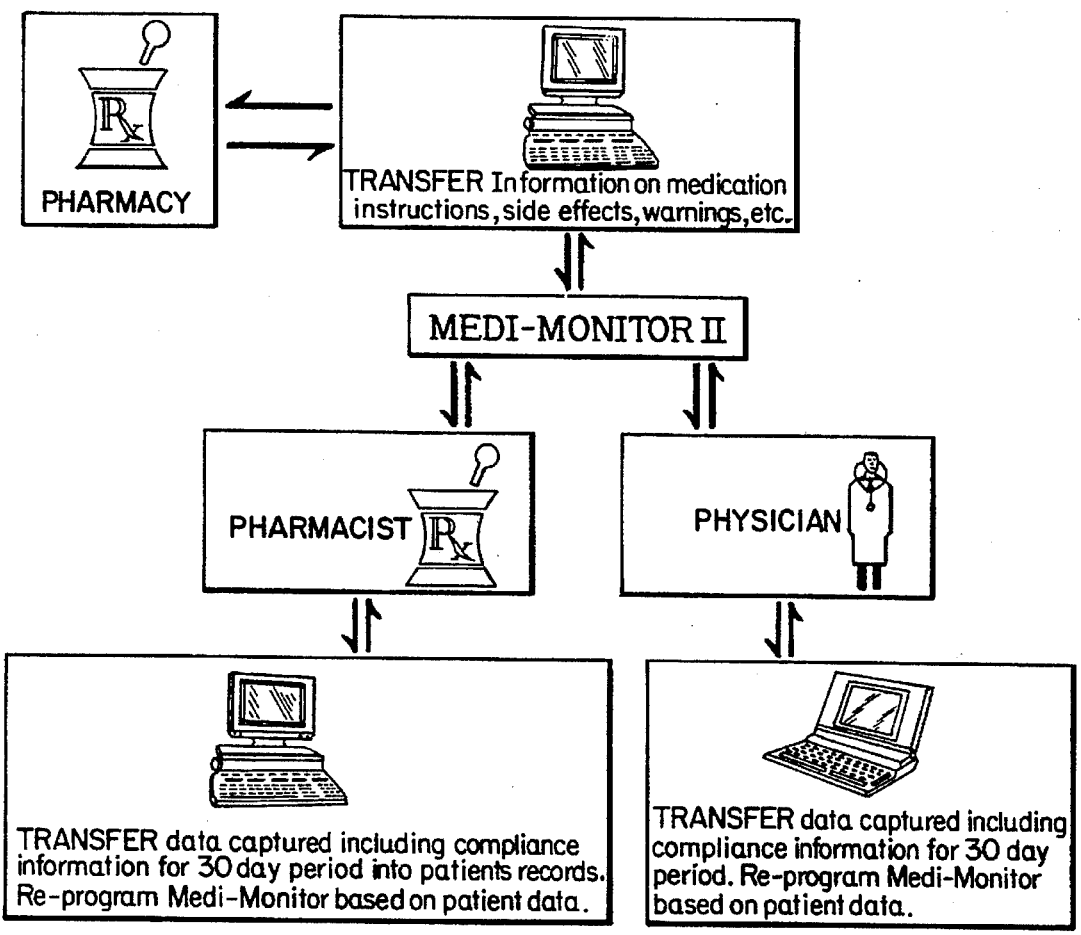
FIG. 2G is a flow diagram showing the cooperation between the computers of the health care professionals and the disease monitoring device of the patient.
Figure 2H:
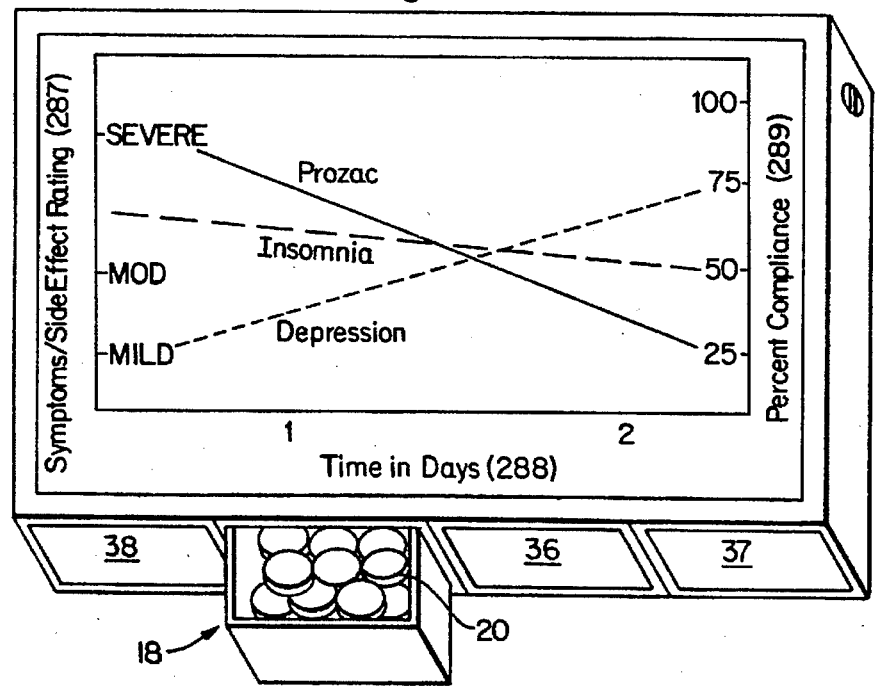
FIG. 2H is a top view of the invention in the act of displaying a graph.

There are a number of other functions and features that such a display can provide the medication dispensing device. By being a programmable screen, information regarding specific drugs or diseases could be uploaded into the medication dispensing device by another computer, or entered via software cartridges. This is shown in FIGS. 2G, and 2B respectively, thus altering the sequencing and type of messages on the screen. In addition, through programmability, such a screen could render its messages in any symbolic language desired. There is obvious commercial advantage to this, in that there could be Spanish speaking, French speaking, Chinese speaking, etc., versions of the software that could be uploaded into one hardware system.

This type of display, incorporated into the device, is not meant to limit the types of displays that might be used with this device. Such a display is available, for example, through the MICROS hand-held touch screen, sold by MICROS Systems, Inc., 1200 Baltimore Avenue, Beltsville, Md. 20705. An example of such a display is their LCD, 120×96 pixel display, dark blue characters on yellow-green anti-glare background. The keyboard is a resistive touch screen overlay. It uses a Mitsubishi 37700 CMOS at 14 MHz, and an EPROM of 256k, with RAM of 512k.

It is desirable to add to the above features additional features that relate to clinical drug trials, and patient management. When assessing clinical outcomes of a particular drug treatment, there are three phases to monitor: the acute phase, the continuation phase, and the maintenance treatment phase. It is desirable to record the above clinical data during each of these phases, so that one can assess how rapidly the patient responds to a particular drug treatment, and assess what the strength of that response is. The rapidity and strength of response can be correlated with the drug compliance data that is recorded by the medication dispensing device. By having the patient record, in realtime, data regarding symptom severity, side-effects severity, general health ratings, and adverse reactions, and to correlate this data with the patient's access to the particular drugs contained within the device, is a substantial improvement over current methods of assessment.

Currently, when patients are being assessed for clinical outcomes, they are given periodic questionnaires to fill in themselves, or to be filled in during a clinical interview. Their compliance is then assessed either by counting the pills that are left in their prescription vials, or by doing blood tests for the blood levels of the medication. It has been well-documented that these methods of assessing compliance are inaccurate. Urquhart et al., U.S. Pat. No. 4,725,997, have developed a prescription bottle cap that records when the cap is removed from a prescription vial, and then makes that data available for downloading. However the disadvantage of this assessment modality is that it cannot be cross-correlated with the patient's clinical state in realtime—i.e., there is no capacity for the device to record symptoms severity, side-effects severity, general health ratings, adverse reactions or other such data in conjunction with compliance data. Such data, when recorded by the patient or the investigator, relies upon the patient's memory which can be faulty.

It is therefore also desirable to display on the touch-screen graphic display 282, summaries of the clinical course of the patient. For example, one could display a graph of how symptom severity is rated over time. The Y axis can be an index of severity for a particular symptom, and the X axis could be dates and times. Likewise, one could display a graph of side-effects severity over time, general health ratings over time, percentage of compliance over time, adverse reactions over time, and could even display all of these clinical data simultaneously to cross-correlate them. As the device captures this data in realtime on an ongoing basis, and as the touch-screen display provides for graphic (in addition to alpha/numeric) displays, the medication dispensing device can display such graphs. This is shown on FIG. 2-H.

The display of such graphs will assist the patient in better medication compliance, and better interactions with his or her doctor. Patients on medication may get frustrated over time, feeling that the medication is not helping them. However, if they see a display of a graph on the device whereby their symptoms are getting better, (albeit they are not yet cured), this will encourage them to continue taking their medication. Likewise, such a graphic display will assist the doctor in readily identifying how a patient is responding to medication. If a patient's symptom severity is not lessening, or worsening, one could then superimpose the graph of compliance data and see whether noncompliance is a factor in causing the lack of improvement in symptoms. It is well-established in compliance literature that compliance is improved to the extent that patients get feedback regarding their medication taking behavior, and effects of medication-taking on the underlying illness. In this regard, a graphic display of the above information will help to improve patient compliance.

There are opportunities for additional types of graphic display as well. A pharmaceutical manufacturer is particularly interested in how compliance with its drugs compares to compliance with its competitor's drugs. As well, the pharmaceutical manufacturer would like to know if its own drugs are more effective than its competitors in treating an underlying illness. The manufacturer would also like to know if its drugs, when taken with other drugs, become more or less effective. The present invention, as distinguished from the prior art, will allow the pharmaceutical manufacturer to make these determinations. All the manufacturer need do is place the present invention out in the field among a number of patients on drug regimens from a number of different manufacturers. The patients will then rate symptom severity, side-effects, general health ratings, adverse reactions, and will also be recording compliance data. The manufacturer will then have access to this data for a wide variety of drugs, in patients who are on multiple medications. This can give the pharmaceutical manufacturer a competitive advantage, by having information on its competitor's drugs to compare to its own drugs. An example of this is shown in FIG. 2-H. Here number 287 shows symptom and side effects ratings, 288 shows time elapsed (in days) and 289 shows the perecent of time the patient is taking the drug correctly. As shown here for Prozac, as compliance declines the depression severity increases and insomnia (a side-effect of Prozac) declines as well.

Finally, all of the above information that is captured and displayed can be downloaded into a computer for further analysis, or to be printed out as shown in FIG. 2-G. A detailed description of how the touch-screen display could be operated is as follows, with explanations of FIGS. 27 through 31. This record could become part of the patient's medical record, or become part of a clinical trials study, or become part of a marketing study to be used by the drug company, or become part of a disease management program where the effectiveness of a particular drug is compared to the effectiveness of competing drugs. As the device simultaneously holds a number of different drugs, and enables the patient to record a variety of clinical and compliance data about the drugs, it offers advantages over any prior art reference.

Figure 27:
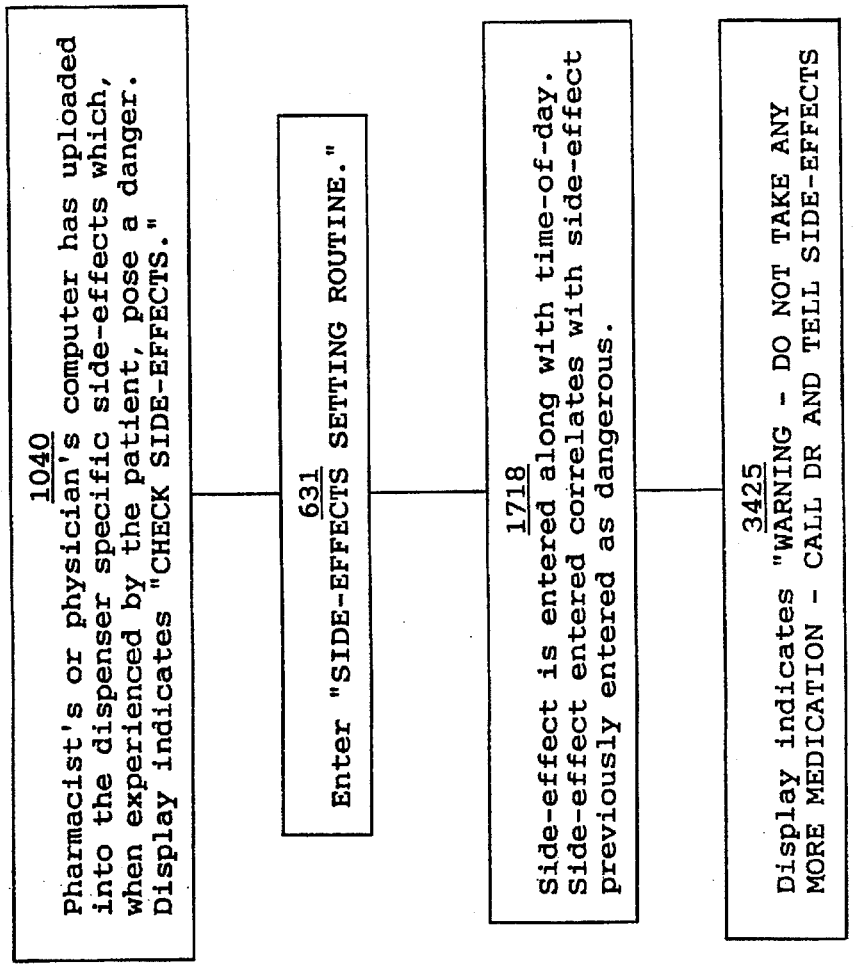
FIG. 27 is a flow chart of the SIDE-EFFECTS DANGER routine.

In the Side Effects Danger Routine of FIG. 27, the pharmacist's or physician's computer has uploaded into the dispenser specific side-effects which, when experienced by the patient, pose a danger. When the patient is entering particular side-effects according to to the side-effects rating routine as shown in Block 631, each side-effect is rated and entered along with the date and time of day as shown in Block 1718, and in FIG. 2D. If one of the entered side-effects correlates with a side-effect that has been uploaded as dangerous, the display indicates "warning—do not take any more medication—call doctor and tell side-effects," and the device gives off a separate alarm.

Figure 28:
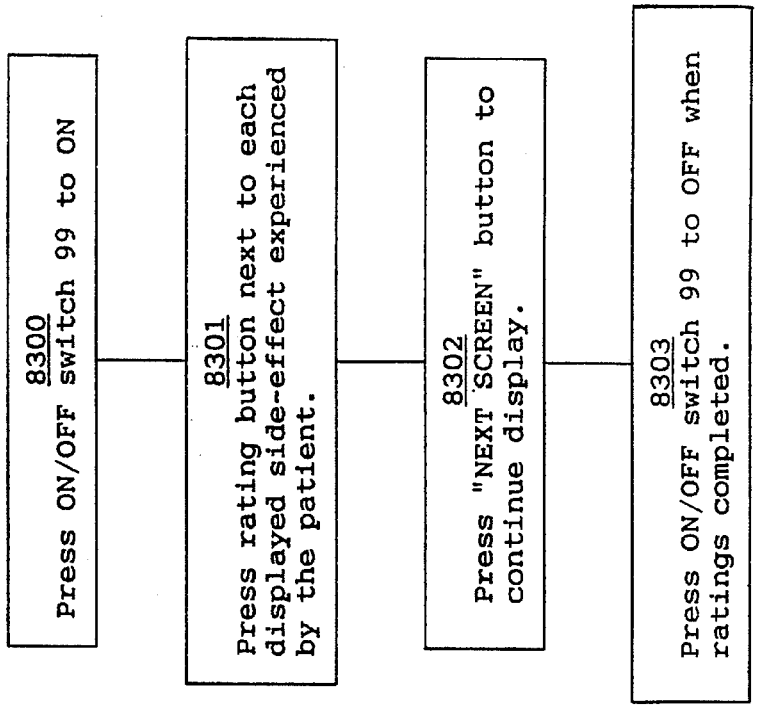
FIG. 28 is a flow chart of the TOUCH-SCREEN SIDE-EFFECTS RATING routine.

In FIG. 28 the Touch-Screen Side-Effects Rating Routine is displayed. Here, the patient presses the "ON/OFF" switch 99 to ON. The device then displays a listing of side-effects, and next to each is a rating scale as noted in Block 8301, and depicted in FIG. 2D. The patient then presses the appropriate rating button on the scale next to each of the displayed side-effects, coinciding with what the patient is experiencing physically. The patient then presses the "NEXT SCREEN" button to continue to the next display of side-effects, which are to be rated. Once the patient has entered all of the side-effects he or she is experiencing, they press the "ON/OFF" switch 99 to OFF and the touch-screen goes blank.

Figure 29:
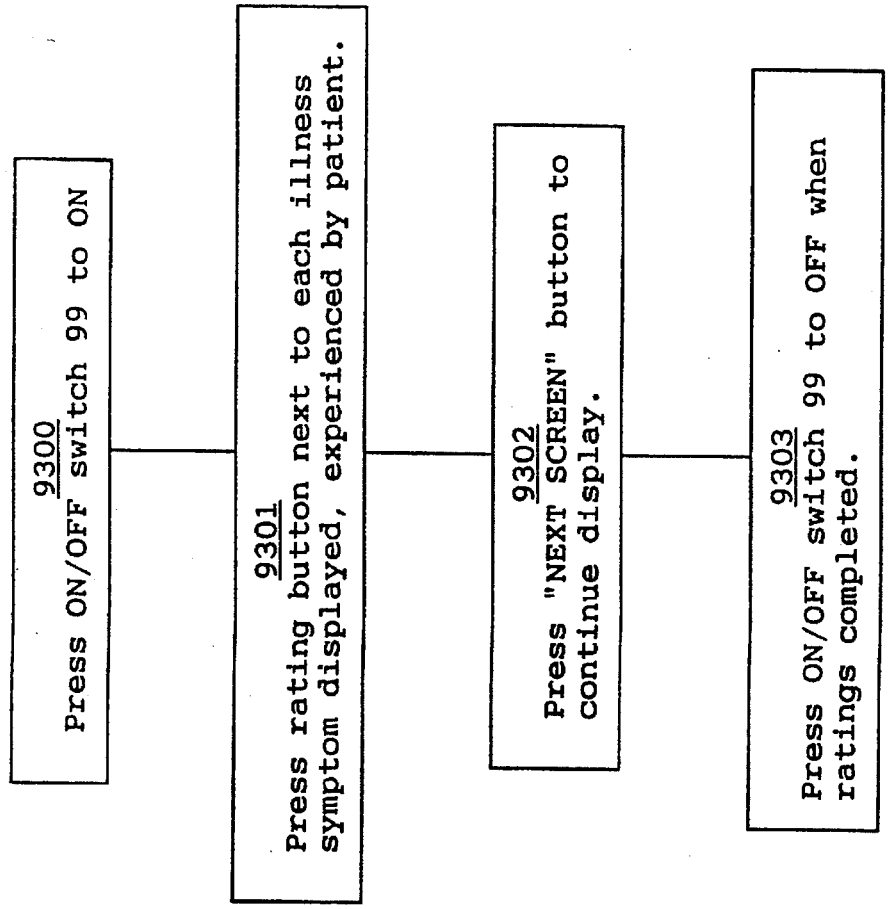
FIG. 29 is a flow chart of the TOUCH-SCREEN ILLNESS SYMPTOM RATING routine.

In FIG. 29 the Touch-Screen Illness Symptom Rating Routine is depicted. The patient presses "ON/OFF" switch 99 to ON. A list of illness symptoms is displayed, and next to each is a rating scale as shown in FIG. 2E, and Block 9301. The patient presses the appropriate rating button next to each illness symptom that they are experiencing. To continue to the next display of symptoms, the patient presses the "NEXT SCREEN" button at the bottom of the screen. When the patient has completed rating all of the illness symptoms that they are experiencing, they press switch 99 to OFF and the screen goes blank.

Figure 30:
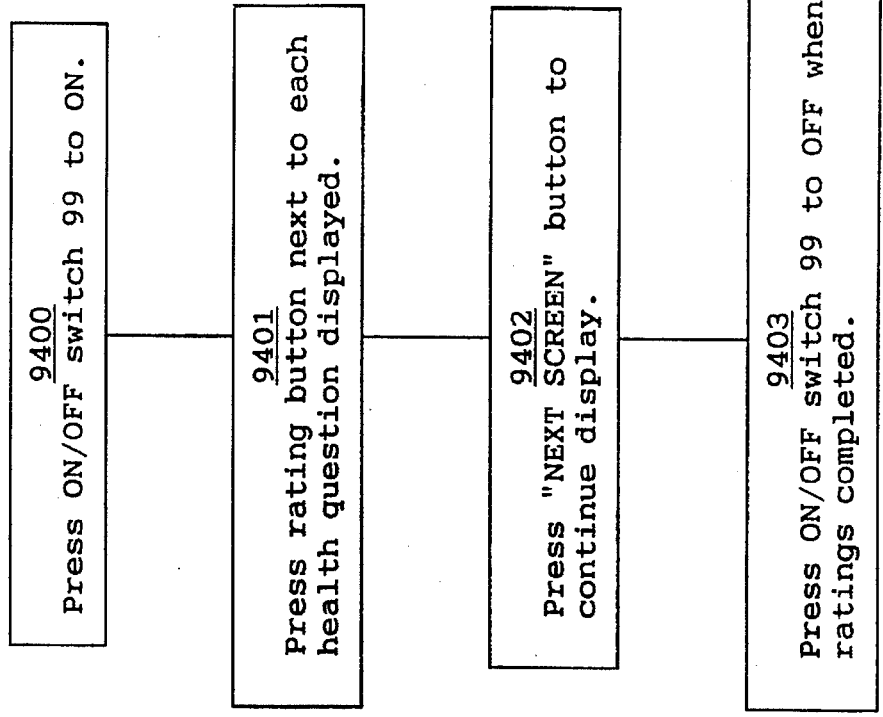
FIG. 30 is a flow chart of the TOUCH-SCREEN GENERAL HEALTH QUESTIONNAIRE routine.

In FIG. 30 the Touch-Screen General Health Questionnaire Routine is displayed. The patient presses the "ON/OFF" button switch 99 to ON. Each general health question is displayed, along with a rating scale next to it as shown in FIG. 2F, and Block 9401. The patient presses the appropriate rating button next to each of the health questions. The patient then presses the "NEXT SCREEN" button to continue the display. When the patient has completed rating all of the health questions, they press switch 99 to "OFF."

In FIG. 31 the Self-Diagnosis Routine is demonstrated. As part of the routine of monitoring the patient's health and illness symptoms, when new symptoms develop, the patient may wish to pursue various self-diagnosis routines that have been preprogrammed into the device. For example, let's say the patient develops a fever. He or she can switch on the device, and the self-diagnosis routine beings with a question "Is your temperature 100° or above?" If the patient answers YES, the display can then display additional questions related to fever, such as "Do you have a sore throat?" "Do you have aching joints?" "Do you have shortness of breath?" And next to each can be buttons for answering "YES" or "NO." Depending upon how the patient answers these questions, it will lead the patient to an "end message" that instructs them whether they should call the doctor, take some aspirin first and then call the doctor, or other such instructions. If the answer to the question regarding the temperature of 100° or above is "NO", the device can branch into a different routine, with a question such as "Have you suddenly begun to feel unusually tired and noticed discomfort in your chest?" If the answer to this is "YES", the patient can be instructed to consult their physician, as they may be having some heart trouble. If the answer to this question is "NO", then further questions can be asked, ultimately leading to an "end message" that will advise the patient. This routine is illustrated in FIG. 31, beginning with Block Diagram 9501. The answers to each of those questions will be stored in the device. They can be cross-correlated with the other information stored, to provide additional "real time" clinical information. For example, if chest pain is correlated with taking too many asthma medications, the doctor can be alerted and assisted in deciding whether it is a medication induced side effect, or a sign that the heart has blocked arteries causing the chest pain.

By recording in real-time these signs and symptoms of newly developing illness, along with medication compliance data, the pharmaceutical manufacturer may uncover new medication side-effects that were previously unreported. Newly developed F.D.A. requirements mandate that these previously unidentified side-effects be reported, yet none of the prior art devices provide this feature. Applicant's device provides a solution.

For the purposes noted below, the word "disease" shall be understood as: a deviation of the body, or an organ of it, from health or normality; a morbid, pathological condition; an illness, sickness or malady; a state of bad health.

I claim to have invented:

1. The method of storing information relating to a patient, comprising:

providing a medical monitoring device, providing said device with a memory for storing information, providing medication for at least one disease, giving take-medication signals at times when said medication should be taken by the patient, storing in said memory a list of responses that may be experienced by the patient's body during the period over which said medication is being taken for said disease, programming said device to display, for the patient, the responses on said list, making a selection, by said patient, of at least one of said responses, and storing a signal in said memory that represents said selection.

2. The method of claim 1, in which said list of responses is a list of symptoms of said disease.

3. A method as defined in claim 2 in which said selecting step comprises selecting one of said symptoms, displaying a plurality of degrees of the severity of the selected symptom, selecting one of said degrees, and entering into said memory said selected degree of severity.

4. The method of claim 1 in which said list of responses is a list of side effects.

5. The method of claim 4 in which said list of side effects includes side effects that may be caused by said medication.

6. A method as defined in claim 4, in which said selecting step comprises selecting a side effect of said medication, displaying a plurality of degrees of the severity of the selected side effect, selecting one of said degrees, and entering into said memory said selected degree of severity.

7. The method of claim 1, comprising storing information regarding one or more of said diseases in said memory.

8. The method of claim 1, further comprising:

providing a second medication for said patient, including in said list one or more adverse reactions that may occur when said first-named medication and said second medication are taken by the patient.

9. The method of claim 8, in which said list of responses includes any reactions that may occur from the taking of two different medications by the patient.

10. The method of claim 1, comprising storing, information relating to the general health of the patient, in said memory.

11. The method of claim 1, comprising storing, a self-diagnosis algorithm, in said memory.

12. The method of claim 1, in which there is a rationale for taking one or more medications, comprising:

storing said rationale in said memory, and displaying said rationale.

13. The method of claim 1, further comprising:

displaying at least one of said selected responses.

14. The method of claim 1, further comprising:

providing a second device, communicating the selected response from said first-named device to said second device.

15. The method of claim 1, comprising:
displaying at least some of said responses at an unscheduled medication time.

16. The method of claim 1, comprising:
displaying at least some of said responses at a time when the patient fails to respond to one of said take-medication signals.

17. The method of claim 1 in which said selected response is a side effect of a medication and
entering into said memory the duration of said side-effect.

18. The method of claim 1, in which said selected response is a symptom of at least one of said diseases, and
entering into said memory the duration of said symptom.

19. The method of claim 1 in which at least one of said responses is a side effect, comprising:
providing a message that is displayed when said side effect is selected.

20. The method of claim 1, in which said list of responses includes symptoms of said disease and also side effects.

21. The method of claim 1 comprising sequentially displaying the responses on said list.

22. The method of claim 1, in which said programming of said device comprises:
programming said device to allow said patient to cause said device to display said list.

23. A device for storing signals representing events that occur during an illness of a patient, comprising:
means including a memory, a timing element and a signaling apparatus, for giving a take-medication signal when medication should be taken for said illness,
means for storing said medication,
said memory including a list of events that may be experienced by a patient who has said illness and who is taking said medication,
means for displaying the events on said list, and
means, for enabling a person to select at least one of said events, and for storing a signal in said memory that represents at least one such selection.

24. A device as defined in claim 23, in which said means for displaying comprises a manually operable means for displaying the events on said list.

25. A device as defined in claim 24, in which said list of responses includes symptoms of said illness.

26. A device as defined in claim 24, comprising:
said means for selecting comprising means for selecting one of said side-effects that was caused by said medication,
means for displaying a plurality of degrees of severity, and
means for selecting one of said degrees and entering a signal in said memory in a manner that records the degree of severity of the selected one of said side effects.

27. A device as defined in claim 23, comprising:
the device having a face, and
means associated with said face for entering information in said memory when said face of the device is touched by a human being.

28. A device as defined in claim 27, in which said face can display a message, said message identifying at least one drug, and at least one other bit of information about said drug.

29. A device as defined in claim 23, including means for making and displaying a picture showing the patient's responses to medication.

30. A device as defined in claim 23, in which said memory comprises means for storing information related to said medication,
said means for displaying comprising means for displaying said information.

31. A device as defined in claim 23 in which said means for storing in said memory a list of events comprises means for storing in said memory a list of events relating to the general health of said patient.

32. A device for storing signals representing a symptom of an illness that occurs during the illness of a patient, comprising:
means including a microprocessor including a memory, a timing element and a signaling apparatus, for giving a take-medication signal when medication should be taken for said illness,
means for storing said medication,
means for storing in said memory a list of responses that may be experienced by a patient after said medication is taken for said illness,
means for displaying the responses on said list, and
means for selecting at least one of said responses and storing a signal in said memory that represents said selection,
said list of responses being a list of symptoms of said illness.

33. A device as defined in claim 32, in which said means for selecting comprises means for selecting one of said symptoms,
means for displaying a plurality of degrees of severity, and
means for selecting one of said degrees and entering a signal in said memory in a manner that records the degree of severity of the selected one of said symptoms.

34. A device for storing signals representing side effects that occur during an illness of a patient comprising:
means including a microprocessor including a memory, a timing element and a signaling apparatus, for giving a take-medication signal when medication should be taken for said illness,
means for storing said medication,
means for storing in said memory a list of responses that may be experienced by a patient after said medication is taken for said illness,
means for displaying the responses on said list, and
means for selecting at least one of said responses and storing a signal in said memory that represents said selection,
said list of responses being a list of side effects.

35. A method of monitoring a disease of a patient, comprising:
providing the patient with a device that receives, stores and gives information,
providing the patient with medication which after it is taken appears in the patient's blood and results in a time at which there is a trough in the patient's blood level of said medication,
providing signals from said device to alert the patient to take said medication for said disease,
providing said device with at least one question that is asked of the patient at about the time of the trough of the patient's blood level of said medication, and
providing said device with means to allow the patient to store the answer to said question in said device.

36. The method of monitoring a disease of a patient, comprising:
providing said patient with a device that will receive, store and display information,
alerting said patient to take medication for said disease,
a user of the device entering into said device signals (1) indicating the amount and type of medication taken by said patient, and (2) reactions, of said patient to either said disease or said medication,
providing apparatus for receiving from said device said signals and for transmitting information to said device,
communicating said signals from said device to said apparatus,
advising the user of the device via said apparatus and said device as to how to further manage said disease.

37. The method of claim 36 in which the patient has information about his or her general health and in which said step of communicating includes communicating signals representing information related to the general health of said patient.

38. The method of claim 36 in which said step of communicating includes communicating information relating to side effects of said medication experienced by said patient.

39. The method of claim 36 in which said step of communicating includes communicating information as to at least one drug interaction experienced by said patient.

40. The method of claim 36, in which said step of entering includes entering information relating to what medication the patient has taken.

41. The method of claim 36 in which said step of entering includes entering a symptom of said disease.

42. The method of claim 36, in which said step of entering includes entering a side effect of the patient's medication and the duration of said side effect.

43. The method of claim 36, in which said patient has a mental attitude and said entering step includes entering information as to the mental attitude of the patient.

44. The method of claim 36, in which said entering step includes entering habits of the patient.

45. The method of claim 36 comprising storing the date and time of entry of said signals.

46. The method of storing a signal relating to a patient, comprising:
providing a medical monitoring device,
providing said device with a memory for storing information,
providing medication for at least one disease,
giving take-medication signals at times when said medication should be taken by the patient,
storing in said memory a list of events that may be experienced by the patient's body during the period over which said medication is being taken for said disease,
displaying, for a user of the device, the events, that are related to the patient's condition, on said list,
selecting, by the user of the device, at least one of said events, that is related to the patient's condition, and
storing a signal in said memory that represents said selection.

47. The method of claim 46, in which said step of storing in said memory a list of events comprises storing in said memory a list of symptoms of said disease.

48. The method of claim 46, in which said step of storing in said memory a list of events comprises storing in said memory a list of side effects.

49. The method of storing information relating to at least one disease of a patient, comprising:
providing a medical monitoring device,
providing said device with a memory for storing information,
providing medication for said disease,
giving take-medication signals at times when said medication should be taken by the patient,
storing in said memory a plurality of events that may be experienced by the patient during the period over which said medication is taken by the patient,
displaying some of said events,
a user of the device selecting at least one of said events that was displayed,
storing signals in said memory that represent at least one of said selected events,
storing in said memory signals that will enable a determination of the date and at least the approximate time of said selection.

50. The method of claim 49, further comprising correlating said signals that enable the determination of said date and at least said approximate time of said selection with the signals that indicate said selected event.

51. The method of claim 49 in which said step of storing in said memory a plurality of events comprises storing in said memory a plurality of symptoms of said disease.

52. The method of claim 49 in which said step of storing in said memory a plurality of events comprises storing in said memory a plurality of side effects of said medication.

53. A device for storing information about a person who has at least one disease, comprising:
a medical monitor which has memory means for storing information,
said medical monitor including means for giving take-medication signals at times when medication should be taken by said person,
said memory means storing signals representing a plurality of events that may be experienced by said person after the taking of said medication,
said medical monitor having means for displaying a plurality of said events,
said medical monitor having means for selecting at least one of the plural events that were displayed,
said memory means storing signals representing each selected event,
said memory means including means for storing signals that will enable a determination of the date and at least the approximate time of said selection.

54. A device as defined in claim 53 in which said medical monitor includes means for correlating said signals that enable a determination of the date and of at least said approximate time of said selection with the signals that indicate which event was selected.

55. A device as defined in claim 53 in which said means for storing in said memory signals representing a plurality of events comprises means for storing in said memory signals representing a plurality of symptoms of said disease.

56. A device as defined in claim 53 in which said means for storing in said memory signals representing a plurality of events comprises means for storing in said memory signals representing a plurality of side effects of said medication.

57. A method of monitoring a disease of a patient, comprising:

providing the patient with a device that receives, stores and gives information, providing the patient with medication which after it is taken appears in the patient's blood and results in a time at which there is a peak in the patient's blood level of said medication, providing signals from said device to alert the patient to take said medication for said disease, providing said device with at least one question that is asked of the patient at about the time of the peak of the patient's blood level of said medication, and providing said device with means to allow the patient to store the answer to said question in said device.

* * * * *